United States Patent
Mayer et al.

(10) Patent No.: US 10,087,545 B2
(45) Date of Patent: Oct. 2, 2018

(54) AUTOMATED CLEANING OF WAFER PLATING ASSEMBLY

(71) Applicant: Novellus Systems, Inc., Fremont, CA (US)

(72) Inventors: Steven T. Mayer, Aurora, OR (US); Thomas A. Ponnuswamy, Sherwood, OR (US); Lee Peng Chua, Beaverton, OR (US); Robert Rash, West Linn, OR (US)

(73) Assignee: Novellus Systems, Inc., Fremont, CA (US)

( * ) Notice: Subject to any disclaimer, the term of this patent is extended or adjusted under 35 U.S.C. 154(b) by 269 days.

(21) Appl. No.: 14/949,681

(22) Filed: Nov. 23, 2015

(65) Prior Publication Data

US 2016/0145761 A1 May 26, 2016

Related U.S. Application Data

(62) Division of application No. 13/563,619, filed on Jul. 31, 2012, now Pat. No. 9,221,081.
(Continued)

(51) Int. Cl.
 B08B 9/00 (2006.01)
 C25D 21/08 (2006.01)
(Continued)

(52) U.S. Cl.
 CPC ............... C25D 21/08 (2013.01); B08B 1/04 (2013.01); C23G 1/02 (2013.01); C25D 21/00 (2013.01);
(Continued)

(58) Field of Classification Search
 CPC ........ C25D 21/08; C25D 21/00; C25D 21/12; B08B 1/04; B08B 1/006; B08B 3/00;
(Continued)

(56) References Cited

U.S. PATENT DOCUMENTS 2,773,257 A 12/1956 Craggs et al.
3,225,899 A 12/1965 Lo Presti et al.
(Continued)

FOREIGN PATENT DOCUMENTS

CN 1509348 A 6/2004
CN 1550033 A 11/2004
(Continued)

OTHER PUBLICATIONS

U.S. Appl. No. 14/936,328, titled "Integrated Elastomeric Lipseal and Cup Bottom for Reducing Wafer Sticking," filed Nov. 9, 2015.
(Continued)

Primary Examiner — Sharidan Carrillo
(74) Attorney, Agent, or Firm — Weaver Austin Villeneuve & Sampson LLP

(57) ABSTRACT

Disclosed herein are cleaning discs for cleaning one or more elements of a semiconductor processing apparatus. In some embodiments, the disc may have a substantially circular upper surface, a substantially circular lower surface, a substantially circular edge joining the upper and lower surfaces, and a plurality of pores opening at the edge and having an interior extending into the interior of the disc. In some embodiments, the pores are dimensioned such that a cleaning agent may be retained in the interior of the pores by an adhesive force between the cleaning agent and the interior surface of the pores. Also disclosed herein are cleaning methods involving loading a cleaning agent into a plurality of pores of a cleaning disc, positioning the cleaning disc within a semiconductor processing apparatus, and releasing cleaning agent from the plurality of pores such that elements of the apparatus are contacted by the released cleaning agent.

22 Claims, 6 Drawing Sheets

Related U.S. Application Data

(60) Provisional application No. 61/513,993, filed on Aug. 1, 2011.

(51) Int. Cl.

| | | |
|---|---|---|
| *B08B 1/04* | (2006.01) | |
| *H01L 21/67* | (2006.01) | |
| *C23G 1/02* | (2006.01) | |
| *C25D 21/00* | (2006.01) | |
| *C25D 21/12* | (2006.01) | |
| *G01N 21/95* | (2006.01) | |
| *B08B 3/00* | (2006.01) | |
| *B08B 1/00* | (2006.01) | |

(52) U.S. Cl.
CPC .... *H01L 21/6723* (2013.01); *H01L 21/67028* (2013.01); *H01L 21/67046* (2013.01); *B08B 1/006* (2013.01); *B08B 3/00* (2013.01); *C25D 21/12* (2013.01); *G01N 21/9501* (2013.01)

(58) Field of Classification Search
CPC .......................... C23G 1/02; G01N 21/9501; H01L 21/67028; H01L 21/67046; H01L 21/6723
See application file for complete search history.

(56) References Cited

U.S. PATENT DOCUMENTS

| | | | |
|---|---|---|---|
| 3,334,750 A * | 8/1967 | Ullman, Jr. | ......... A47L 15/4204 |
| | | | 134/111 |
| 3,430,055 A | 2/1969 | Metzger | |
| 3,684,633 A | 8/1972 | Haase | |
| 3,716,765 A | 2/1973 | Rueffer et al. | |
| 3,724,471 A | 4/1973 | Sitges | |
| 4,418,432 A | 12/1983 | Vidal | |
| 4,466,864 A | 8/1984 | Bacon et al. | |
| 4,569,695 A | 2/1986 | Yamashita et al. | |
| 4,654,235 A | 3/1987 | Effenberger et al. | |
| 4,924,891 A | 5/1990 | Soubrier et al. | |
| 5,000,827 A | 3/1991 | Schuster et al. | |
| 5,221,449 A | 6/1993 | Colgan et al. | |
| 5,227,041 A | 7/1993 | Brogden et al. | |
| 5,281,485 A | 1/1994 | Colgan et al. | |
| 5,289,639 A | 3/1994 | Bard et al. | |
| 5,311,634 A | 5/1994 | Andros | |
| 5,482,611 A | 1/1996 | Helmer et al. | |
| 5,519,945 A | 5/1996 | Ahvenniemi et al. | |
| 5,723,028 A | 3/1998 | Poris | |
| 5,853,559 A | 12/1998 | Tamaki et al. | |
| 5,860,361 A | 1/1999 | Nanjyo et al. | |
| 5,985,762 A | 11/1999 | Geffken et al. | |
| 6,071,388 A | 6/2000 | Uzoh | |
| 6,074,544 A | 6/2000 | Reid et al. | |
| 6,080,291 A | 6/2000 | Woodruff et al. | |
| 6,099,702 A | 8/2000 | Reid et al. | |
| 6,108,847 A | 8/2000 | Cueman et al. | |
| 6,110,346 A | 8/2000 | Reid et al. | |
| 6,124,203 A | 9/2000 | Joo et al. | |
| 6,126,798 A | 10/2000 | Reid et al. | |
| 6,139,712 A | 10/2000 | Patton et al. | |
| 6,156,167 A | 12/2000 | Patton et al. | |
| 6,159,354 A | 12/2000 | Contolini et al. | |
| 6,162,344 A | 12/2000 | Reid et al. | |
| 6,176,985 B1 | 1/2001 | Downes, Jr. et al. | |
| 6,179,973 B1 | 1/2001 | Lai et al. | |
| 6,179,983 B1 | 1/2001 | Reid et al. | |
| 6,193,854 B1 | 2/2001 | Lai et al. | |
| 6,217,716 B1 | 4/2001 | Lai | |
| 6,221,757 B1 | 4/2001 | Schmidbauer et al. | |
| 6,251,238 B1 | 6/2001 | Kaufman et al. | |
| 6,251,242 B1 | 6/2001 | Fu et al. | |
| 6,261,433 B1 | 7/2001 | Landau | |
| 6,267,860 B1 | 7/2001 | Brodsky | |
| 6,270,646 B1 | 8/2001 | Walton et al. | |
| 6,274,008 B1 | 8/2001 | Gopalraja et al. | |
| 6,277,249 B1 | 8/2001 | Gopalraja et al. | |
| 6,303,010 B1 | 10/2001 | Woodruff et al. | |
| 6,309,520 B1 | 10/2001 | Woodruff et al. | |
| 6,309,981 B1 | 10/2001 | Mayer et al. | |
| 6,379,468 B1 | 4/2002 | Chang et al. | |
| RE37,749 E | 6/2002 | Poris | |
| 6,398,926 B1 | 6/2002 | Mahneke | |
| 6,413,388 B1 | 7/2002 | Uzoh et al. | |
| 6,436,249 B1 | 8/2002 | Patton et al. | |
| 6,517,689 B1 | 2/2003 | Hongo et al. | |
| 6,540,899 B2 | 4/2003 | Keigler | |
| 6,551,487 B1 | 4/2003 | Reid et al. | |
| 6,579,430 B2 | 6/2003 | Davis et al. | |
| 6,589,401 B1 | 7/2003 | Patton et al. | |
| 6,612,915 B1 | 9/2003 | Uzoh et al. | |
| 6,613,214 B2 | 9/2003 | Dordi et al. | |
| 6,627,052 B2 | 9/2003 | Fluegel et al. | |
| 6,755,946 B1 | 6/2004 | Patton et al. | |
| 6,755,954 B2 | 6/2004 | Mayer et al. | |
| 6,773,560 B2 | 8/2004 | Pedersen et al. | |
| 6,800,187 B1 | 10/2004 | Reid et al. | |
| 6,869,510 B2 | 3/2005 | Woodruff et al. | |
| 6,908,540 B2 | 6/2005 | Kholodenko | |
| 7,033,465 B1 | 4/2006 | Patton et al. | |
| 7,070,686 B2 | 7/2006 | Contolini et al. | |
| 7,087,144 B2 | 8/2006 | Herchen | |
| 7,285,195 B2 | 10/2007 | Herchen et al. | |
| 7,522,055 B2 | 4/2009 | Carrender et al. | |
| 7,935,231 B2 | 5/2011 | Ghongadi et al. | |
| 7,985,325 B2 | 7/2011 | Rash et al. | |
| 8,172,992 B2 | 5/2012 | Prabhakar et al. | |
| 8,377,268 B2 | 2/2013 | Rash et al. | |
| 8,398,831 B2 | 3/2013 | Ghongadi et al. | |
| 9,221,081 B1 * | 12/2015 | Mayer | ...................... C23G 1/02 |
| 9,228,270 B2 | 1/2016 | Feng et al. | |
| 9,476,139 B2 | 10/2016 | Chua et al. | |
| 9,746,427 B2 * | 8/2017 | Mayer | ............... G01N 21/9501 |
| 2001/0020480 A1 | 9/2001 | Yoshikawa et al. | |
| 2002/0000372 A1 | 1/2002 | Pedersen et al. | |
| 2002/0020763 A1 | 2/2002 | Hirae et al. | |
| 2002/0084183 A1 | 7/2002 | Hanson et al. | |
| 2002/0108851 A1 | 8/2002 | Woodruff et al. | |
| 2002/0134403 A1 | 9/2002 | Selwyn et al. | |
| 2002/0144900 A1 | 10/2002 | Keigler | |
| 2002/0153260 A1 | 10/2002 | Egli et al. | |
| 2002/0157686 A1 | 10/2002 | Kenny et al. | |
| 2003/0010641 A1 | 1/2003 | Kholodenko | |
| 2003/0085118 A1 | 5/2003 | Tench et al. | |
| 2003/0085119 A1 | 5/2003 | Davis et al. | |
| 2003/0134044 A1 | 7/2003 | Aoki et al. | |
| 2003/0181349 A1 | 9/2003 | Maeno et al. | |
| 2003/0201184 A1 | 10/2003 | Dordi et al. | |
| 2004/0002430 A1 | 1/2004 | Verhaverbeke | |
| 2004/0060576 A1 | 4/2004 | Cronin et al. | |
| 2004/0084301 A1 | 5/2004 | Dordi et al. | |
| 2004/0112405 A1 | 6/2004 | Lee et al. | |
| 2004/0149573 A1 | 8/2004 | Herchen | |
| 2004/0171277 A1 | 9/2004 | Oh et al. | |
| 2005/0081899 A1 | 4/2005 | Shannon | |
| 2005/0183947 A1 | 8/2005 | Henuset | |
| 2005/0218000 A1 | 10/2005 | Hafezi et al. | |
| 2005/0284754 A1 | 12/2005 | Herchen et al. | |
| 2005/0287928 A1 | 12/2005 | Hardikar et al. | |
| 2006/0113192 A1 | 6/2006 | Kurashina et al. | |
| 2006/0118132 A1 | 6/2006 | Bergman et al. | |
| 2006/0151007 A1 | 7/2006 | Bergman | |
| 2006/0226000 A1 | 10/2006 | Hanson et al. | |
| 2006/0237308 A1 | 10/2006 | Herchen | |
| 2006/0246690 A1 | 11/2006 | Dordi et al. | |
| 2006/0266653 A1 | 11/2006 | Birang et al. | |
| 2007/0077871 A1 | 4/2007 | Park et al. | |
| 2007/0141849 A1 | 6/2007 | Kanno et al. | |
| 2007/0199578 A1 | 8/2007 | Nomura et al. | |
| 2008/0011322 A1 | 1/2008 | Weber et al. | |
| 2008/0117051 A1 | 5/2008 | Carrender et al. | |
| 2009/0009753 A1 | 1/2009 | Horai et al. | |
| 2009/0033889 A1 | 2/2009 | Bleeker et al. | |

(56) References Cited

U.S. PATENT DOCUMENTS

| | | | |
|---|---|---|---|
| 2009/0107835 | A1 | 4/2009 | Ghongadi et al. |
| 2009/0107836 | A1 | 4/2009 | Rash et al. |
| 2009/0117730 | A1 | 5/2009 | Maitani et al. |
| 2010/0116290 | A1 | 5/2010 | Zhu et al. |
| 2010/0144158 | A1 | 6/2010 | Ito et al. |
| 2010/0155254 | A1 | 6/2010 | Prabhakar et al. |
| 2010/0216302 | A1 | 8/2010 | Luo et al. |
| 2011/0181000 | A1 | 7/2011 | Ghongadi et al. |
| 2011/0233056 | A1 | 9/2011 | Rash et al. |
| 2012/0043200 | A1 | 2/2012 | Fujikata et al. |
| 2012/0137970 | A1 | 6/2012 | Naruse et al. |
| 2012/0181170 | A1 | 7/2012 | Prabhakar et al. |
| 2013/0042454 | A1 | 2/2013 | Feng et al. |
| 2013/0062197 | A1 | 3/2013 | He et al. |
| 2013/0256146 | A1 | 10/2013 | Chua et al. |
| 2013/0292254 | A1 | 11/2013 | Kumar et al. |
| 2014/0230855 | A1* | 8/2014 | Mayer ............... G01N 21/9501 134/18 |
| 2014/0367265 | A1 | 12/2014 | Ravid et al. |
| 2015/0218726 | A1 | 8/2015 | Feng et al. |
| 2016/0145761 | A1* | 5/2016 | Mayer ............... C23G 1/02 134/26 |
| 2016/0186355 | A1 | 6/2016 | Feng et al. |
| 2016/0201212 | A1 | 7/2016 | Ostrowski et al. |
| 2017/0009369 | A1 | 1/2017 | Berke et al. |
| 2017/0009370 | A1 | 1/2017 | Chua et al. |
| 2017/0073832 | A1 | 3/2017 | Berke et al. |
| 2017/0299524 | A1* | 10/2017 | Arora ............... G01N 21/9515 |

FOREIGN PATENT DOCUMENTS

| | | |
|---|---|---|
| CN | 1623012 A | 6/2005 |
| CN | 1930666 A | 3/2007 |
| CN | 100469948 C | 3/2009 |
| CN | 101599420 | 12/2009 |
| CN | 101798698 A | 8/2010 |
| CN | 102953104 A | 3/2013 |
| CN | 103031580 A | 4/2013 |
| EP | 1 724 820 A1 | 11/2006 |
| JP | 2002-069698 | 3/2002 |
| JP | 2002-540011 | 11/2002 |
| JP | 2004-83932 | 3/2004 |
| JP | 2004-247738 | 9/2004 |
| JP | 2004-270014 | 9/2004 |
| JP | 2005-146398 | 6/2005 |
| JP | 2007-204832 | 8/2007 |
| JP | 2008-045179 | 2/2008 |
| JP | 2008-95157 | 4/2008 |
| KR | 10-2004-0079843 | 9/2004 |
| KR | 10-2004-0081577 | 9/2004 |
| KR | 10-2005-0068038 | 7/2005 |
| KR | 10-2007-0064847 | 6/2007 |
| KR | 10-2008-0007931 | 1/2008 |
| TW | 531770 | 5/2003 |
| TW | 544811 | 8/2003 |
| TW | 200409836 | 6/2004 |
| TW | 200410296 A | 6/2004 |
| TW | 200511422 A | 3/2005 |
| TW | I244548 | 12/2005 |
| TW | 2009/16796 A | 4/2009 |
| TW | I585246 B | 6/2017 |
| WO | WO 99/041434 | 8/1999 |
| WO | WO 03/006718 | 1/2003 |
| WO | WO 03/010368 A | 2/2003 |
| WO | WO 2013/148890 | 10/2013 |

OTHER PUBLICATIONS

U.S. Appl. No. 13/563,619, titled "Automated Cleaning of Wafer Plating Assembly," filed Jul. 31, 2012.
U.S. Office Action, dated Nov. 1, 2011, issued in U.S. Appl. No. 12/633,219.
U.S. Notice of Allowance, dated Jan. 12, 2012, issued in U.S. Appl. No. 12/633,219.
U.S. Notice of Allowance, dated Mar. 19, 2012, issued in U.S. Appl. No. 12/633,219.
U.S. Office Action, dated Oct. 26, 2012, issued in U.S. Appl. No. 13/432,767.
U.S. Final Office Action, dated Nov. 26, 2013, issued in U.S. Appl. No. 13/432,767.
U.S. Office Action, dated Nov. 6, 2014, issued in U.S. Appl. No. 13/563,619.
U.S. Final Office Action, dated Apr. 23, 2015, issued in U.S. Appl. No. 13/563,619.
U.S. Notice of Allowance, dated Aug. 31, 2015, issued in U.S. Appl. No. 13/563,619.
U.S. Notice of Allowance [corrected Notice of Allowability], dated Sep. 23, 2015, issued in U.S. Appl. No. 13/563,619.
U.S. Office Action, dated Feb. 23, 2015, issued in U.S. Appl. No. 13/584,343.
U.S. Notice of Allowance, dated Aug. 31, 2015, issued in U.S. Appl. No. 13/584,343.
U.S. Office Action, dated Mar. 2, 2011, issued in U.S. Appl. No. 11/929,638.
U.S. Notice of Allowance, dated May 23, 2011, issued in U.S. Appl. No. 11/929,638.
U.S. Office Action, dated Jul. 7, 2010, issued in U.S. Appl. No. 11/932,595.
U.S. Office Action, dated Nov. 17, 2010, issued in U.S. Appl. No. 11/932,595.
U.S. Notice of Allowance, dated Jan. 26, 2011, issued in U.S. Appl. No. 11/932,595.
U.S. Notice of Allowance, dated Mar. 8, 2011, issued in U.S. Appl. No. 11/932,595.
U.S. Notice of Allowance (Supplemental Notice of Allowability) dated Mar. 11, 2011, issued in U.S. Appl. No. 11/932,595.
U.S. Notice of Allowance, dated Mar. 18, 2011, issued in U.S. Appl. No. 11/932,595.
U.S. Office Action, dated Nov. 4, 2011, issued in U.S. Appl. No. 13/154,224.
U.S. Office Action, dated Mar. 16, 2012, issued in U.S. Appl. No. 13/154,224.
U.S. Final Office Action, dated Jul. 18, 2012, issued in U.S. Appl. No. 13/154,224.
U.S. Notice of Allowance, dated Oct. 4, 2012, issued in U.S. Appl. No. 13/154,224.
U.S. Notice of Allowance (Corrected Notice of Allowability) dated Jan. 23, 2013, issued in U.S. Appl. No. 13/154,224.
U.S. Office Action, dated May 21, 2012, issued in U.S. Appl. No. 13/079,745.
U.S. Office Action, dated Sep. 21, 2012, issued in U.S. Appl. No. 13/079,745.
U.S. Notice of Allowance, dated Nov. 19, 2012, issued in U.S. Appl. No. 13/079,745.
U.S. Office Action, dated Oct. 28, 2015, issued in U.S. Appl. No. 13/852,767.
Chinese First Office Action dated May 2, 2013 issued in CN 200910211989.X.
Japanese Office Action, dated Oct. 2, 2012, issued in Application No. 2009-278998.
Korean Description of Notification of Provisional Rejection, dated May 10, 2012, issued in Application No. 2009-0122738.
Korean Notification of Decision to Grant, dated Sep. 4, 2012, issued in Application No. 2009-0122738.
Singapore Search Report and Written Opinion, dated Mar. 9, 2011, issued in Application No. 200908245.4.
Singapore Search and Examination Report, dated Oct. 27, 2011, issued in Application No. 200908245.4.
Taiiwan International Search Report, dated Jun. 11, 2012, issued in Application No. 098142112.
Singapore Search Report and Written Opinion, dated Oct. 6, 2014, issued in Application No. 201206129-7.
Singapore Final Exam Report, dated May 20, 2015, issued in Application No. 201206129-7.

(56) References Cited

OTHER PUBLICATIONS

PCT International Search Report and Written Opinion dated Jul. 25, 2013 issued in PCT/US2013/034178.
PCT International Preliminary Report on Patentability and Written Opinion dated Oct. 9, 2014 issued in PCT/US2013/034178.
Everett, D.H. (2001) "Definition of Surface Active Agents," *Manual of Symbols and Terminology for Physicochemical Quantities and Units, Appendix II, International Union of Pure and Applied Chemistry, Division of Physical Chemistry*, Adopted by the IUPAC Council at Washington DC, USA on Jul. 23, 1971, 6pp.
Shin-Etsu Polymer Co., Ltd., "L-type connector," http://www.shinpoly.co.jp./business/connector/products_e/l/html?typezeb (one page) downloaded May 23, 2003.
Shin-Etsu Polymer Co., Ltd., "SS-type connector," http://www.shinpoly.co.jp./business/connector/products_e/ss.html?typezeb (2 pages) downloaded May 23, 2003.
Zheng, CN 101599420a, abstract and machine translation (2009).
U.S. Office Action, dated Nov. 23, 2016, issued in U.S. Appl. No. 14/178,804.
U.S. Notice of Allowance, dated May 3, 2017, issued in U.S. Appl. No. 14/178,804.
U.S. Notice of Allowance [Corrected Notice of Allowability], dated Jul. 21, 2017, issued in U.S. Appl. No. 14/178,804.
U.S. Office Action, dated Mar. 6, 2017, issued in U.S. Appl. No. 14/685,526.
U.S. Notice of Allowance, dated Aug. 7, 2017, issued in U.S. Appl. No. 14/685,526.
U.S. Notice of Allowance, dated Feb. 6, 2018, issued in U.S. Appl. No. 14/685,526.
U.S. Office Action, dated Sep. 21, 2017, issued in U.S. Appl. No. 14/990,725.
U.S. Notice of Allowance, dated Sep. 1, 2017, issued in U.S. Appl. No. 14/936,328.
U.S. Notice of Allowance, dated Apr. 12, 2018, issued in U.S. Appl. No. 14/936,328.
U.S. Office Action, dated Oct. 31, 2017, issued in U.S. Appl. No. 15/004,593.
U.S. Office Action, dated Sep. 7, 2017, issued in U.S. Appl. No. 14/957,156.
U.S. Final Office Action, dated Mar. 21, 2018, issued in U.S. Appl. No. 14/957,156.
U.S. Notice of Allowance, dated Jun. 30, 2016, issued in U.S. Appl. No. 13/853,935.
U.S. Final Office Action, dated Apr. 28, 2016, issued in U.S. Appl. No. 13/852,767.
U.S. Office Action, dated Feb. 24, 2017, issued in U.S. Appl. No. 13/852,767.
U.S. Final Office Action, dated Aug. 25, 2017, issued in U.S. Appl. No. 13/852,767.
Japanese Decision to Grant w/Search Report dated Mar. 27, 2018 issued in Application No. JP 2014-026848.
Chinese First Office Action dated Jun. 20, 2017 issued in Application No. CN 201510837221.9.
Chinese Second Office Action dated Feb. 24, 2018 issued in Application No. CN 201510837221.9.
Chinese First Office Action dated Jan. 26, 2016, issued in Application No. CN 201210289735.1.
Chinese Second Office Action dated Nov. 2, 2016, issued in Application No. CN 201210289735.1.
Japanese First Office Action dated Jun. 28, 2016, issued in Application No. JP 2012179853.
Japanese Second Office Action dated Mar. 14, 2017, issued in Application No. JP 2012-179853.
Taiwan Office Action and Search Report, dated May 12, 2016, issued in Application No. TW 101129602.
Taiwan Office Action, dated Jul. 11, 2017, issued in Application No. TW 106105154.
Taiwan Notice of Allowance and Search Report, dated Sep. 8, 2017, issued in Application No. TW 102111465.
Chinese First Office Action dated Mar. 2, 2016 issued in Application No. CN 201380023757.6.
Chinese Second Office Action dated Jan. 24, 2017 issued in Application No. CN 201380023757.6.
Taiwan Examination and Search Report dated Oct. 12, 2016, issued in TW 102111233.
Chinese First Office Action dated Jan. 29, 2018, issued in CN 201610539196.0.
Cambridge English Dictionary, Meaning of "against" (2016), 2 pages.
DuPont Teflon, Dupont, May 2015, 5pp [Downloaded on Oct. 11, 2017 at https://web.archive.org/web/20150301000000*https://plastics.ulprospector.com/generics/41/c/t/polyphenylene-sulfide-pps-properties-processing].
Guide to Whitford Industrial Coatings 2012, Whitford Worldwide, 3pp [Downloaded on Oct. 11, 2017 at https://web.archive.org/web/*/http://efpadm2.itum.com/files/files/rpn/7.pdf] (Year: 2012).
Merriam-Webster Dictionary, Definition of "Integrate" [Downloaded on Aug. 28, 2017 at https://www.merriam-webster.com/dictionary/integrate], 12pp.
Wikipedia, the free encyclopedia, Definition of "Through hole" [Downloaded on Aug. 24, 2017 from https://en.wikipedia.org/wiki/Through_hole, 1 page.
Notice of Allowance dated May 1, 2018 issued in U.S. Appl. No. 14/990,724.
U.S. Final Office Action dated May 11, 2018 issued in U.S. Appl. No. 15/004,593.

\* cited by examiner

US 10,087,545 B2

AUTOMATED CLEANING OF WAFER PLATING ASSEMBLY

CROSS-REFERENCE TO RELATED APPLICATIONS

This application is a divisional of and claims priority to U.S. patent application Ser. No. 13/563,619, filed Jul. 31, 2012, titled "AUTOMATED CLEANING OF WAFER PLATING ASSEMBLY," now, U.S. Pat. No. 9,221,081, which claims the benefit of U.S. Provisional Patent Application No. 61/513,993, filed Aug. 1, 2011, titled "AUTOMATED CLEANING OF WAFER PLATING ASSEMBLY," all of which are incorporated herein by reference in their entireties for all purposes.

TECHNICAL FIELD

The present disclosure relates to apparatuses and methods for cleaning a semiconductor holding and processing apparatus and, in particular, for removing unwanted metal deposits from a wafer handling and processing apparatus and, even more particularly, from a plating assembly.

BACKGROUND

Electrochemical deposition may be employed at various points in the integrated circuit (IC) fabrication and packaging processes. At the IC chip level, damascene features are created by electrodepositing/plating copper within vias and trenches to form multiple interconnected metallization layers. Above the multiple metallization layers, the "packaging" of the chip begins. Various wafer level packaging ("WLP") structures may be employed, some of which contain alloys or other combinations of two or more metals or other components. For example, the packaging may include one or more "bumps" made from solder or related materials. A typical example of a plated bump starts with a conductive substrate seed layer (e.g. a copper seed layer) having an "under bump" diffusion layer of plated nickel (e.g. 1-2 µm thick and about 100 µm wide) under a film of lead tin solder plated pillar (e.g. 50-100 µm thick and about 100 µm wide). After plating, photoresist stripping, and etching of the conductive substrate copper seed layer, the pillar of solder is carefully melted or "reflowed" to create a solder "bump" or ball attached to the under bump metal.

As an alternative to this scheme (often referred to as "copper pillar" or "micro pillar"), an under bump of a non-solder plated "pillar" metal such as copper, nickel, or a combination of these two, is created below a typically much thinner and smaller solder film than above. In this scheme, useful in achieving tight/precise feature pitch and separation control, the copper pillars may be for example 50 µm or less in width, features separated from one another by 75-100 µm center to center, and the copper may be 20-40 µm in height. On top of the copper pillar, a nickel barrier film, e.g., about 1-2 µm thick, is sometime used to separate the copper from the tin containing solder and thereby avoid a solid state reaction to form various mechanically and chemical undesirable bronzes. Finally, a solder layer, typically 20-40 µm in thickness is added. This scheme also enables a reduced amount of solder for the same features size, reducing cost or total amount of lead (in lead containing solders) in the chip.

Lead-tin materials provide good quality "bumps" for packaging and are very easy to plate. Unfortunately, environmental and health-safety concerns regarding lead's toxicity is driving a movement away from the use of lead containing solders. For example, the RoHS initiative (Directive 2002/95/EC of The European Parliament) requires entities to change from the established tin-lead process to a lead free one. Logical replacement bump materials include indium, tin, tin-silver binary materials, tin-bismuth binary materials, and tin-silver-copper ternary materials. Materials based upon tin alone can suffer from a number of fundamental limitations and application difficulties, such as the tendency to form large single grained balls with varying crystal orientations and thermal expansion coefficients, and "tin whiskers" which can lead to interconnect-to-interconnect shorting. The binary and tertiary materials may perform better and alleviate some of these pure tin issues, potentially, at least in part, by precipitating a large number of small grain inclusions of the non-tin component as part of the solder melt to solid state freezing process. Certain compositions made from silver-tin alloys, may demonstrate these characteristics. Thus, silver-tin solder alloy bumps are of particular interest.

SUMMARY OF THE INVENTION

Disclosed herein are cleaning discs for cleaning one or more elements of a semiconductor holding and processing apparatus. In some embodiments, the disc may have a substantially circular upper surface, a substantially circular lower surface, a substantially circular edge joining the upper and lower surfaces, and a plurality of pores opening at the edge and having an interior extending into the interior of the disc. In some embodiments, the pores are dimensioned such that a cleaning agent may be retained in the interior of the pores by an adhesive force between the cleaning agent and the interior surface of the pores. In certain such embodiments, the edge may have an upper portion joined to the upper surface of the disc as well as a lower portion joined to the lower surface of the disc which has a radius less than the radius of the upper portion. The openings of the plurality of pores may be located in this lower portion of the edge, and in some embodiments, the mean height of the lower portion of the cleaning disc's edge may be about or between 0.5 mm and 3.0 mm. In some embodiments, the diameter of the disc is about or between 150 mm and 500 mm. In some embodiments, the cleaning disc may be constructed at least partially from a corrosion resistant metal such as stainless steel, titanium, or tantalum. In some embodiments, the cleaning disc may be constructed at least partially from a corrosion resistant thermoplastic polymer such as a polycarbonate, or polyphenylene sulfide or polyvinylidene fluoride.

In some embodiments, the plurality of pores may have substantially circular openings, and in certain such embodiments, the pores may be drilled holes. In some embodiments, the substantially circular openings may have diameters about or between 0.25 mm and 1.25 mm. In some embodiments, an interior surface of the pores may be hydrophilic.

In some embodiments, the cleaning disc may include a cleaning agent adsorbent element which, in some embodiments, is composed at least partially of a fibrous, and/or cloth-like, and/or filter material for retaining the cleaning agent. The adsorbent element may be configured to supply cleaning agent to the plurality of pores.

Also disclosed herein are methods of cleaning one or more elements of a semiconductor holding and processing apparatus. In some embodiments, the methods include loading a cleaning agent into a cleaning disc by receiving the cleaning agent into a plurality of pores within one or more edges of the cleaning disc, holding the cleaning agent inside the plurality of pores, positioning the cleaning disc within the processing apparatus such that the plurality of pores are adjacent to the one or more elements of the apparatus to be cleaned (the one or more elements to be cleaned normally being adjacent to a semiconductor wafer when a wafer is held in the processing apparatus for processing), and releasing cleaning agent from the plurality of pores such that the one or more elements of the apparatus to be cleaned are contacted by the released cleaning agent. In some embodiments, the method of cleaning may be used to clean a semiconductor holding and processing apparatus after the apparatus has been used to electroplate a semiconductor wafer.

In certain embodiments, the cleaning methods disclosed herein may further include removing cleaning agent from one or more outside surfaces of the cleaning disc, after the loading step just described, but prior to the positioning step just described. In certain such embodiments, such removal of cleaning agent may include spinning the disc at a rotation rate such that cleaning agent flows off the outside surfaces of the disc, but cleaning agent substantially remains within the plurality of pores, such as, for example, at a rotation rate about or between 50 RPM and 250 RPM. In certain such embodiment methods, the viscosity of the rinsing agent may be less than the viscosity of the cleaning agent.

In certain cleaning methods disclosed herein, loading the cleaning agent in the cleaning disc may include immersing a portion of the cleaning disc in the cleaning agent, and may further include drawing the cleaning agent into the pores by capillary action. In certain cleaning methods disclosed herein, holding the cleaning agent may further include adhering the cleaning agent to the interior surfaces of the plurality of pores.

In certain cleaning methods disclosed herein, releasing cleaning agent from the cleaning disc's plurality of pores may include spinning the disc at a rotation rate such that the one or more elements of the semiconductor holding and processing apparatus to be cleaned are contacted by the released cleaning agent, but the released cleaning agent does not substantially flow continuously out of the plurality of pores. In certain embodiments, a cleaning method may further include sucking cleaning agent back into the cleaning disc's plurality of pores, after the cleaning agent was released to contact the one or more elements of the semiconductor holding and processing apparatus to be cleaned. In certain such embodiments, suction is created by reducing the rotation rate of the disc relative to the rotation rate used for releasing cleaning agent. The cleaning methods disclosed herein may further include removing the cleaning disc from the processing apparatus, and unloading cleaning agent from the plurality of pores by spinning the disc. In some embodiment methods, the disc may be spun at a rotation rate of about or greater than 500 rpm to unload cleaning agent form the plurality of pores.

Cleaning methods disclosed herein may be used to clean various elements of a semiconductor holding and processing apparatus. In some embodiments, the one or more elements of the processing apparatus to be cleaned include the lip seal of the processing apparatus, and/or the cup bottom of the processing apparatus. In some embodiments, the cleaning method removes metal deposits from one or more elements of the semiconductor holding and processing apparatus. In certain such embodiments, the metal deposits may include an alloy of tin and/or an alloy of indium.

Cleaning methods disclosed herein may employ a variety of cleaning agents. In some embodiments, a cleaning method may include an acid as a cleaning agent. In certain such embodiments, the acid may be nitric acid, and it may have a concentration in the cleaning agent of about 10% or more by weight. In some embodiments, the cleaning agent may include a metal complexing agent.

DETAILED DESCRIPTION

Figure 1A:
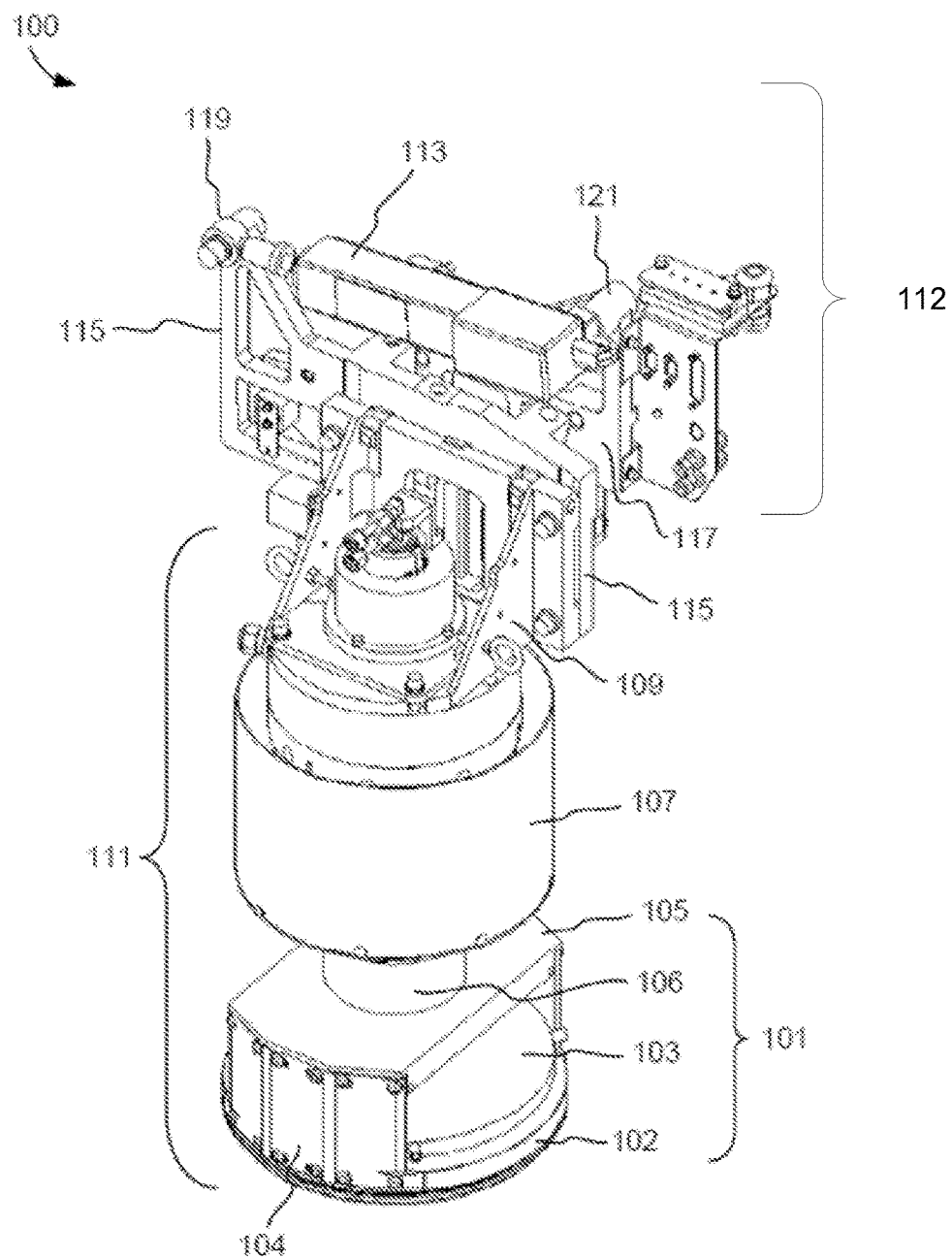
FIG. 1A is a perspective view of a substrate handling and processing apparatus.

Deposition of silver-tin alloys is accomplished by a challenging process that frequently employs an inert anode (rather than the potentially more desirable "active" or soluble anode). Part of the difficulty in using an active anode for this and similar systems results from the very widely separated electrochemical deposition potentials of silver and tin; the standard electrochemical potentials ($E_0$s) of the metals are separated by more than 0.9 volts ($Ag^+$/Ag: 0.8V NHE, $Sn^{+2}$/Sn: −0.15V). Since elemental silver is substantially more noble and inert than elemental tin, it will therefore undergo a displacement reaction and electroplate out of solution onto the surface of a tin anode or tin/silver anode. This chemical "short circuit" removes (strips or extracts) the relatively low concentration of silver from the plating solution continuously, resulting in both an uncontrollable process as well as the formation of reduced silver metal on the tin anode.

Methods and apparatuses for efficient and high-quality plating when using potential-differing set of metals are described in U.S. Patent Application No. 61/502,590, filed Jun. 29, 2011, entitled "ELECTRODEPOSITION WITH ISOLATED CATHODE AND REGENERATED ELECTROLYTE," naming Steven T. Mayer as inventor; U.S. Patent Application No. 61/418,781, filed Dec. 1, 2010, entitled, "ELECTROPLATING APPARATUS AND PROCESS FOR WAFER LEVEL PACKAGING," naming Steven T. Mayer, et al. as inventors; and U.S. patent application Ser. No. 13/172,642, filed Jun. 29, 2011, entitled, "CONTROL OF ELECTROLYTE HYDRODYNAMICS FOR EFFICIENT MASS TRANSFER DURING ELECTROPLATING," naming Steven T. Mayer et al, as inventors; each of which is hereby incorporated by reference in their entirety herein for all purposes. Despite the existence of relatively good quality plating regimes for plating two or more metals, when there is a large difference in the plating potentials of the metals unwanted metal oftentimes plates out on surfaces of the wafer holder and/or handler. Thus there remains the question of how to deal with these unwanted metal deposits. Although the discussion herein is frequently couched in terms of silver tin plating, the principles discussed apply equally well to any unwanted deposits. That is, the methods and apparatuses disclosed herein may be used for dealing generally with unwanted metal or even non-metal deposits.

Accordingly, described herein are methods and apparatuses for cleaning wafer handling and processing equipment, and in particular handing and processing equipment that holds and rotates a semiconductor wafer during processing. The processing may involve plating or any other semiconductor fabrication process which leaves unwanted material deposited on the wafer handling and processing equipment. In some embodiments, the unwanted material to be removed from various elements of the apparatus are metal deposits. In certain such embodiments, the metal deposits include an alloy of tin, or more particularly an alloy of tin and silver, or still more particularly an alloy of tin, silver, and copper. In some embodiments, the metal deposits may include an alloy of tin and bismuth, or an alloy of indium, or more particularly an alloy of tin and indium. In some embodiments, the cleaning apparatus removes unwanted material deposits from the portion of the wafer handling and processing equipment which is near the semiconductor wafer when loaded for processing. In some embodiments, the unwanted metal to be removed has been deposited on the wafer handling and processing equipment in close proximity to the edge of the semiconductor wafer, where it could potentially interfere with further processing of the wafer or subsequent wafers.

FIG. 1A provides a perspective view of a wafer handling and processing apparatus 100 for electrochemically treating (e.g. electroplating) semiconductor wafers, to which the disclosed cleaning methods and apparatuses may be applied. Note that although FIG. 1A illustrates a particular wafer handling and processing apparatus, the cleaning methods and apparatus disclosed herein may be applied to a variety of pieces of wafer handling and processing equipment, and so the instant disclosure is not limited in application to that which is disclosed in FIG. 1A.

Wafer handling and processing apparatus 100 has various features which are illustrated in FIG. 1A and also described with respect to subsequent Figures. Apparatus 100 includes a semiconductor wafer engaging component which may be referred to as a "clamshell." A clamshell may include a cup 102 and also a cone 103 which may clamp a semiconductor wafer securely in the cup 102.

In FIG. 1A, the cup 102 is supported by struts 104, which are connected to a top plate 105. This assembly 102-105, collectively cup/cone assembly 101, is driven by a motor 107, via a spindle 106. Motor 107 is attached to a mounting bracket 109. The spindle 106 transmits torque to a semiconductor wafer (not shown in this figure) being held/engaged by the cup/cone assembly 101 so that the wafer rotates during treatment (e.g. electroplating). Inside spindle 106 there may be an air cylinder (not visible in FIG. 1A) which provides a vertical force clamping the wafer between the cup 102 and cone 103. The entire assembly of components referenced as 102-109 (which includes the cup/cone assembly) is collectively referred to as wafer holder 111 in FIG. 1A. Note, however, that the concept of a "wafer holder" extends generally to various combinations and sub-combinations of components for engaging/holding a wafer and/or for providing mechanisms for its movement and positioning.

Also illustrated in FIG. 1A, is a tilting assembly 112, which may include a first plate 115 slidably connected to a second plate 117. The first plate 115 is also connected to a mounting bracket 109 which is located on the distal end of the wafer holder 111. Also illustrated in FIG. 1A is a drive cylinder 113 connected to both the first plate 115 and the second plate 117 at pivot joints 119 and 121, respectively. Thus, the drive cylinder 113 may provide a drive force for sliding plate 115 across plate 117, thus positioning semiconductor wafer holder 111. The distal end of wafer holder 111 (the end having the mounting bracket 109) thus may be moved along an arced path defined by the contact region between plates 115 and 117, and therefore the proximal end of wafer holder 111 having the cup/cone assembly may be tilted with respect to a virtual pivot point. In some embodiments, this allows for the angled entry of the semiconductor wafer into a treatment solution (e.g. an electroplating bath).

The entire apparatus 100 is lifted vertically either up or down to immerse the proximal end of wafer holder 111 into a treatment solution via another actuator (not shown). Thus, a two-component positioning mechanism provides both vertical movement along a trajectory perpendicular to a treatment solution (e.g. an electrolytic electroplating bath), and also a tilting movement allowing the position of the wafer to deviate from a horizontal orientation relative to the surface of the treatment solution thus providing an angled-wafer immersion capability. A more detailed description of the movement capabilities and associated hardware of apparatus 100 is described in U.S. Pat. No. 6,551,487, filed May 31, 2001, issued Apr. 22, 2003, and titled "METHODS AND APPARATUS FOR CONTROLLED-ANGLE WAFER IMMERSION," which is hereby incorporated herein by reference in its entirety for all purposes.

Note that during electroplating, apparatus 100 is typically used with a particular plating cell having a plating chamber which houses an anode and an electrolyte. The plating cell may also include plumbing or plumbing connections for circulating electrolyte through the plating cell, and against the wafer being electroplated. The plating cell may also include membranes or other separators designed to maintain different electrolyte chemistries in an anode compartment versus a cathode compartment.

Figure 1B:
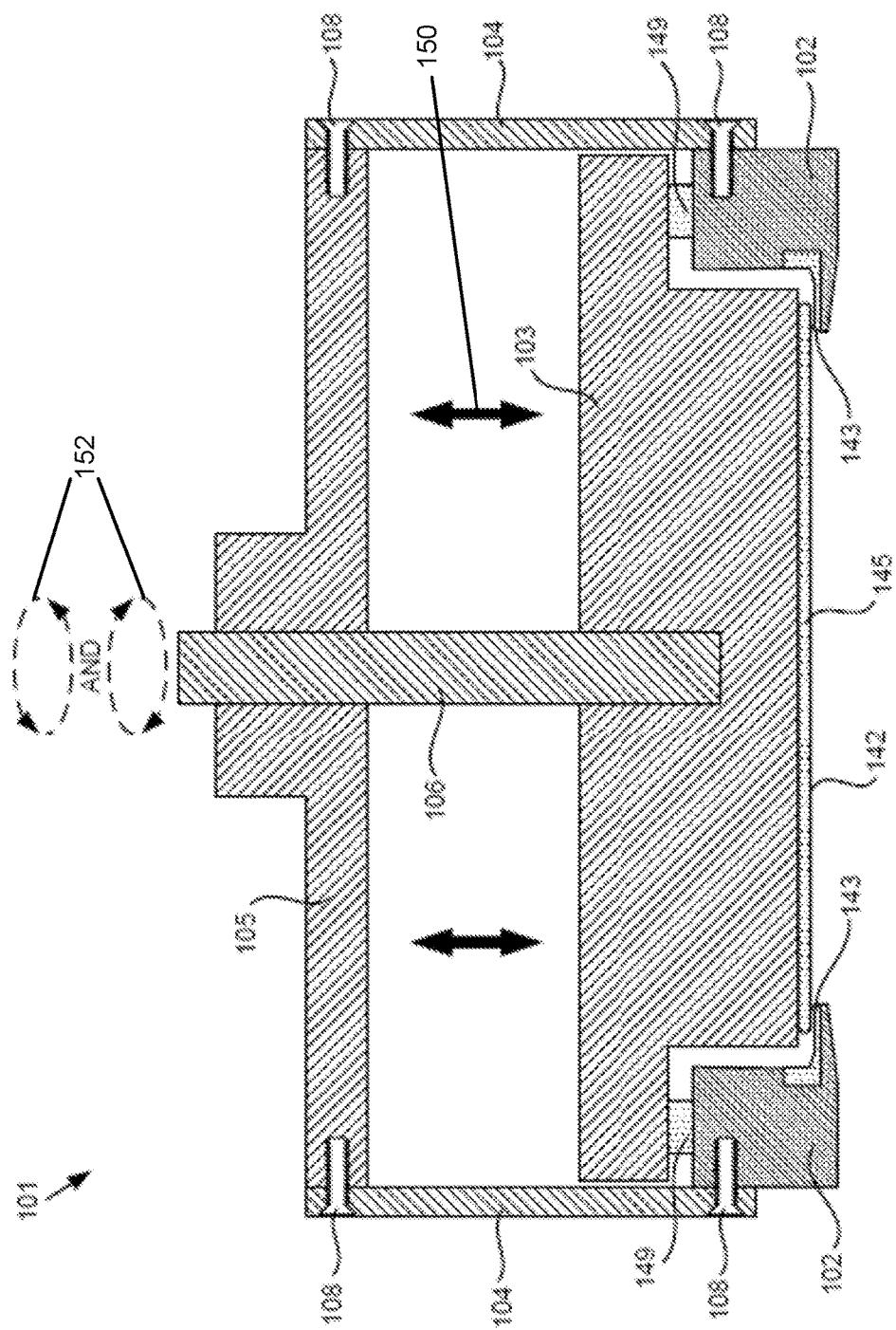
FIG. 1B is a cross-sectional view of a cup/cone clamshell assembly holding a semiconductor wafer.

FIG. 1B provides a more detailed view of the cup/cone assembly 101, including a cross-sectional view of cup 102 and cone 103. Note that the cup/cone assembly 101 depicted in FIG. 1B is not intended to be proportionately accurate, but rather is an exhibit stylized to promote the clarity of the following description. Cup 102 is supported by top plate 105 via struts 104, which are attached via screws 108. Generally, a wafer 145 rests on cup 102 which is configured to support it. Cup 102 also includes an opening through which a treatment solution (e.g. an electrolyte) from the treatment cell (e.g. an electroplating cell) may contact the wafer. Note that the wafer treatment generally takes place on the front side 142 of wafer 145 which, for example, is where the electroplating would occur. Thus, the periphery of wafer 145 rests on the cup 102. Cone 103 presses down on the back side of the wafer 145 to engage it and hold it in place during a treatment process such as electroplating. Once engaged, treatment solution may be generally substantially prevented from contacting the back side of the wafer 145.

To load a wafer 145 into cup/cone assembly 101, cone 103 is lifted from its depicted position via spindle 106 until there is a sufficient gap between the cup 102 and the cone 103 to allow insertion of wafer 145 into the cup/cone assembly 101. The wafer 145 is then inserted, in some embodiments by a robot arm, and allowed to rest lightly on the cup 102 (or on a related component attached to the cup, such as a lip seal 143 as described below). In some embodiments, the cone 103 is lifted from its depicted position until it touches top plate 105. Subsequently, the cone 103 is then lowered to press and engage the wafer against the periphery of cup 102 or attached lip seal 143 as depicted in FIG. 1B. In some embodiments, the spindle 106 transmits both a vertical force for causing the cone 103 to engage the wafer 145, and also the torque for rotating the cup/cone assembly 101 as well as the wafer 145 being held by the cup/cone assembly. FIG. 1B indicates the directionality of the vertical force and rotational orientation of the torque by solid arrows 150 and dashed arrows 152, respectively. In some embodiments, electroplating of the wafer 145 typically occurs while the wafer 145 is rotating. In certain such embodiments, rotating the wafer 145 during electroplating aids in achieving uniform plating.

In some embodiments, such as that depicted in FIG. 1B, cup 102 includes a lip seal 143, which forms a substantially fluid-tight seal against the wafer 145 when cone 103 engages wafer 145. In some embodiments, the lip seal 143 is compressible. In some embodiments, vertical force from the cone 103 presses the wafer 145 against the cup 102 and lip seal 143, compressing the lip seal 143 so as to form a substantially fluid tight seal. Thus, when engaged, the lip seal 143 generally substantially prevents treatment solution (e.g. an electrolytic electroplating solution) from reaching and contacting the backside of wafer 145 (where it could contaminate the wafer such as by introducing contaminating metal atoms directly into the exposed silicon on the backside). This sealing also generally prevents treatment solution from contacting the sensitive components of apparatus 101. In some embodiments, there may also be an additional seal 149 located between the cup 102 and the cone 103, which engages the surfaces of the cup 102 and cone 103 to generally form a substantially fluid-tight seal when the cone 103 engages the wafer 145. The additional sealing provided by cup/cone seal 149 functions to further protect the backside of the wafer 145. Cup/cone seal 149 may be affixed to either the cup 102, or to the cone 103, engaging the alternative element when the cone 103 engages the wafer 145. Cup/cone seal 149 may be a single component seal or a multi-component seal. Similarly, lip seal 143 may be a single component seal or a multi-component seal. Furthermore, a variety of materials may be used to construct seals 143 and 149, as would be appreciated by one of ordinary skill in the art. For instance, in some embodiments, the lip seal is constructed of an elastomeric material, and in certain such embodiments, a perfluoropolymer.

As outlined above, electroplating a lead-free solder alloy, such as, for example a lead-free tin-silver alloy, tends to raise a variety of technical issues—some of which relate to the potential contamination and resulting required clean-up of the wafer processing apparatus used for electroplating. Many of these issues are driven by the propensity of the electroplating bath to: (1) sensitize the wafer supporting lip seal 143 and cup 102 by exposure to stannous tin (i.e. tin having a +2 charge), and (2) cause a displacement reaction involving the tin and silver ions in the plating bath, whereby spuriously deposited/plated tin metal is replaced with plated silver metal. In turn, the displacement of plated tin with plated silver leads to: (1) a volume increase in spurious deposited metal by virtue of the differential volumes of tin and silver deposits, and (2) increased corrosion resistance and resistance to cleaning by virtue of the higher chemical stability of the deposited silver metal. In some circumstances, these effects can cause a rapid buildup of spurious metal deposits on the cup 102 and on the lip seal 143 of the cup, potentially leading to catastrophic failure of the apparatus's ability to perform intended functions. Spurious plating on the cup and sealing elements alters current distribution in the wafer and causes a loss of process control.

The current state of the art for handling the problem of spurious metal deposits, and in particular, spurious deposits of tin-silver alloy, is to periodically replace various cup and lip seal holding elements (e.g. the lip seal and or cup bottom) that have accumulated spurious deposits. However, periodic replacement of the cup and/or lip seal introduces significant cost and loss of productivity. Also, even when cleaning these elements is possible, manual maintenance with cleaning agents increases the potential for cup and/or lip seal damage, excessive tool down-time, loss of productivity, and potential exposure of tool operators and maintenance personal to both the electroplating bath and to potentially noxious cleaning chemicals. Thus, in some embodiments, the apparatuses and methods disclosed herein may address these problems by automating the selective cleaning and removal of unwanted metal deposits.

Accordingly, embodiments described herein include apparatuses for cleaning and removing spurious metal deposits from one or more elements of a semiconductor processing/treatment apparatus, and in particular removing spurious metal deposits from a plating apparatus. In some embodiments, the one or more elements to be cleaned include the lip seal of the treatment apparatus, as well as the bottom cup region near the lip seal of the semiconductor treatment apparatus. In one embodiment, the apparatus is a swab configured to be applied to the area proximate the cup bottom and lip seal. The swab may hold a cleaning agent that removes the unwanted metal deposits and selectively applies the agent to the desired area. The swab may be configured to allow for easy wetting of the surfaces of the lip seal and cup bottom but to avoid encroachment into and damage of the inner sections of the cup including the wafer contact regions of the cup bottom and lip seal. In certain such embodiments, a robotic arm may manipulate the swab and carry out the cleaning operation.

In another embodiment, the apparatus for cleaning and removing spurious metal deposits is a disk shaped apparatus that can fit into a wafer holder assembly in place of a semiconductor wafer. Such a cleaning disc may be configured to deliver cleaning agents to the area around the circumference of the wafer holding and positioning assembly, e.g. the lip seal and cup areas proximate the circumference of the wafer during plating. In certain embodiments, the cleaning disc is configured to absorb, retain, or otherwise hold a cleaning agent, and, when appropriate, deliver the cleaning agent to the wafer cup holder and sealing area (e.g. the cup bottom and lip seal). In certain embodiments, the cleaning agent is retained by an adhesive force between the cleaning agent and one or more surfaces of the cleaning disc. In certain such embodiments, delivery of cleaning agent to the cup bottom, lip seal, and/or to any other region of the treatment apparatus proximate to the circumference of a wafer during plating occurs without substantially introducing the cleaning agent into other parts of the treatment apparatus—e.g., into the plating bath.

Also disclosed herein are methods for cleaning one or more elements of a wafer treatment apparatus. In some embodiments, the methods may be automated. In some embodiments, the methods employ the use of a cleaning swab. In other embodiments, the methods employ the use of a cleaning disc. These methods may promote tool up-time, improve the quality of cleaning operations, and also help to prevent damage to the cup bottom and lip seal which may occur as a result of manual wipe-down chemical treatment of the wafer contact region.

In some embodiments, selection of the cleaning agent will depend on the composition of the unwanted deposits to be removed. For instance, removal of unwanted tin-silver alloy deposits, may successfully employ an oxidizing acid solution into which both tin and silver metal and salts are oxidizable and/or soluble. Thus, in some embodiments, the cleaning agent may include an acid and/or oxidizing agent. A particular example of an appropriate cleaning agent or cleaning solution for removing tin-silver alloy deposits may thus be a solution of nitric acid. Such a solution may have, for example, a nitric acid concentration of about or greater than 5%, 10%, 15%, 20%, 25%, 35%, or 50% by weight; or about or less than any one of these concentrations; or within a range defined by any pair of these concentrations. In some embodiments, a cleaning agent/solution may employ multiple acids, such as, for instance, a combination of nitric acid and hydrochloric acid (i.e. to form aqua regia) with both acids present in any of the above recited concentrations or within the above recited ranges of concentrations. However, other acids and combinations of acids may also be employed—again, in any of the above recited concentrations or recited ranges of concentrations. In some embodiments, the cleaning agent may be a metal complexing agent, and typically a complexing agent selected for it's ability to complex a metal making up the deposits to be removed. For instance, a complexing agent selected as a cleaning agent may be oxalate ion since it complexes tin. In some embodiments, a silver complexing agent may be selected as a cleaning agent, such as various mercapto-derivative compounds.

In some embodiments, the apparatus for cleaning and removing spurious metal deposits from one or more elements of a semiconductor processing apparatus takes the form of a disk shaped apparatus dimensioned such that it can take the place of a semiconductor wafer loaded in the processing apparatus's wafer holder assembly. In certain such embodiments, this cleaning disk is used to clean the cup bottom and lip seal areas, and is referred to as a "cup and lip-seal cleaning disc" or "CLSCD" for short. In some embodiments, the diameter of the cleaning disc is approximately the same as that of a standard semiconductor wafer. Thus, the cleaning disc may have a diameter of about 150 mm, 200 mm, 250 mm, 300 mm, 350 mm, 400 mm, 450 mm, or 500 mm, or the cleaning disc's diameter may fall within a range defined by any pair of these recited diameters. By having an approximate shape and thickness similar to that of a standard semiconductor wafer, the cleaning disc may be suitably handled and moved through a wafer treatment environment, such as, for example, moved by a robotic wafer handler arm of a plating tool to and from various stations within the plating tool. In one embodiment, the cleaning disc may be stored within the tool, for example, in a standard wafer storage area of the tool, when the cleaning disc is not in use. In other embodiments, the cleaning disc is loaded from a plating tool as if it were a normal wafer to be processed/plated, i.e. run and processed from the tool loading location, and returned to the wafer storage area after processing.

Figure 2A:
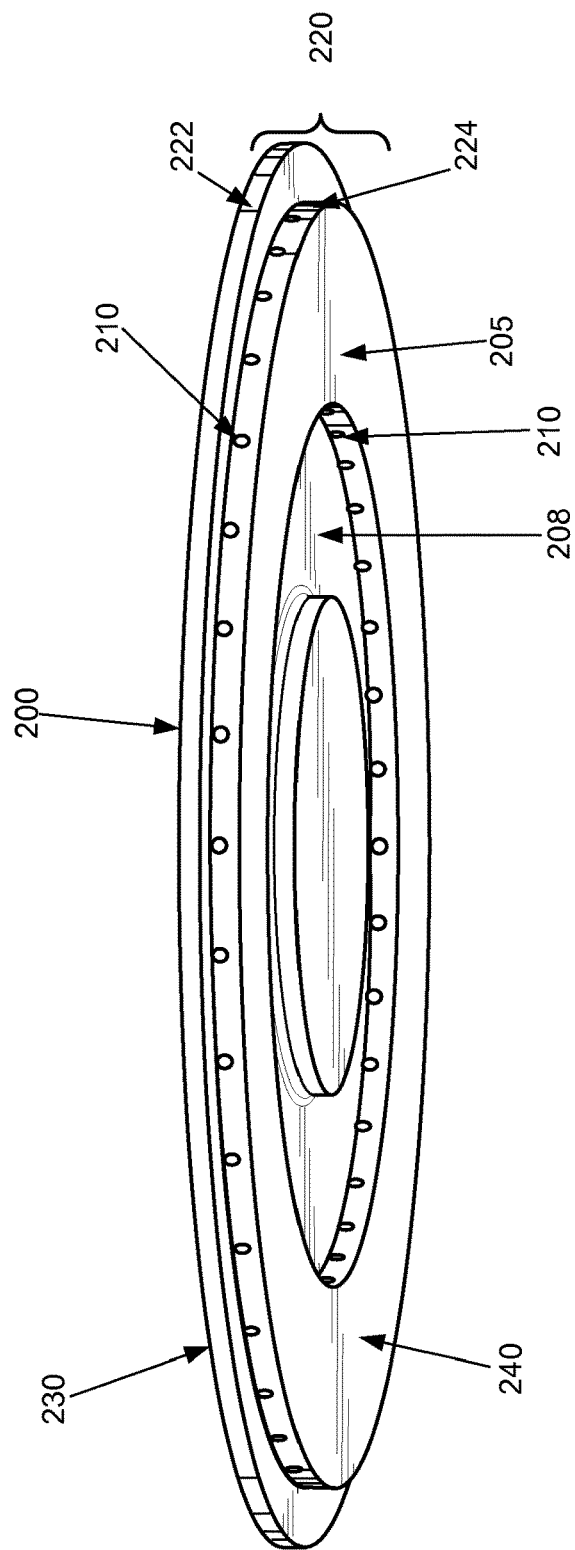
FIG. 2A is a perspective view of one embodiment of a cleaning disc viewed from below.

One embodiment of a cleaning disc is schematically illustrated in FIG. 2A, which shows a perspective view of this embodiment from below. Note that FIG. 2A displays an exemplary embodiment, presented for explanatory purposes—it should not be construed in any manner which limits the various aspects of the inventions disclosed herein. The cleaning disc 200 may have a substantially circular upper surface 230, a substantially circular lower surface 240, a substantially circular edge 220 joining the upper and lower surfaces, 230 and 240, and one or more features 210 allowing the cleaning disc 200 to retain a cleaning agent. In some embodiments, the cleaning disc may have a plurality of pores 210 opening at the circular edge 220 (which joins the upper and lower surfaces, 230 and 240). The pores 210 may have an interior extending into the interior of the disc 200, and be dimensions such that a cleaning agent may be retained in the interior of the pores 210 by an adhesive force between the cleaning agent and the interior surface of the pores 210. Depending on the embodiment, at the appropriate time and/or conditions the cleaning agent is released from the cleaning disc 200 so that one or more elements of the treatment apparatus are contacted by the cleaning agent in order to remove unwanted deposits therefrom. In certain such embodiments having a plurality of pores, cleaning agent is released from the interior surface of the pores.

In some embodiments, the cleaning disc 200 is a self-contained unit, configured to be pre-loaded with a cleaning agent and then inserted into the wafer holder in order to carry out the cleaning operation. The cleaning disc may have a cleaning agent reservoir 208 configured to supply the dispensing features of the cleaning disc such that more than one cleaning operation may be performed before reloading/resupplying the cleaning disc with cleaning agent. In other embodiments, the cleaning disc is reloaded/resupplied with cleaning agent for each cleaning operation.

The cleaning disc may be constructed of a variety of different types of materials, so long as the cleaning disc is made from materials chemically and mechanically compatible with its intended use. In some embodiments, the cleaning disc is primarily made from a corrosion resistant metal such as a suitable grade of stainless steel (e.g., 304, 316), or titanium, or tantalum, or appropriate alloys, for example. In certain such embodiments, the surface of the metal may be coated with a protective polymer film. In certain embodiments, it stands to reason that a sufficiently protective polymer film may facilitate the use of a less corrosion resistant metal as well. In other embodiments, the cleaning disc may be primarily made from a corrosion resistant thermoplastic polymer. A suitable variety of polymer may be a hard, stiff, generally crystalline and/or cross-linked polymer that is chemically resistant to one or more appropriate cleaning agents, such as strongly acidic and oxidizing process chemicals, and also to the corrosive chemicals oftentimes used in plating baths as described above and in more detail below. Suitable polymers include Ryton/Techron, polyphenylene sulfide (PPS), and polyvinylidene fluoride (PVDF), and in some cases Lexan™ or similar polycarbonates. Thus, in some embodiments, the cleaning disc is made from a corrosion resistant thermoplastic polymer such as a polycarbonate, polyphenylene sulfide, polyvinylidene fluoride, or some combination of the foregoing.

Figure 2B:
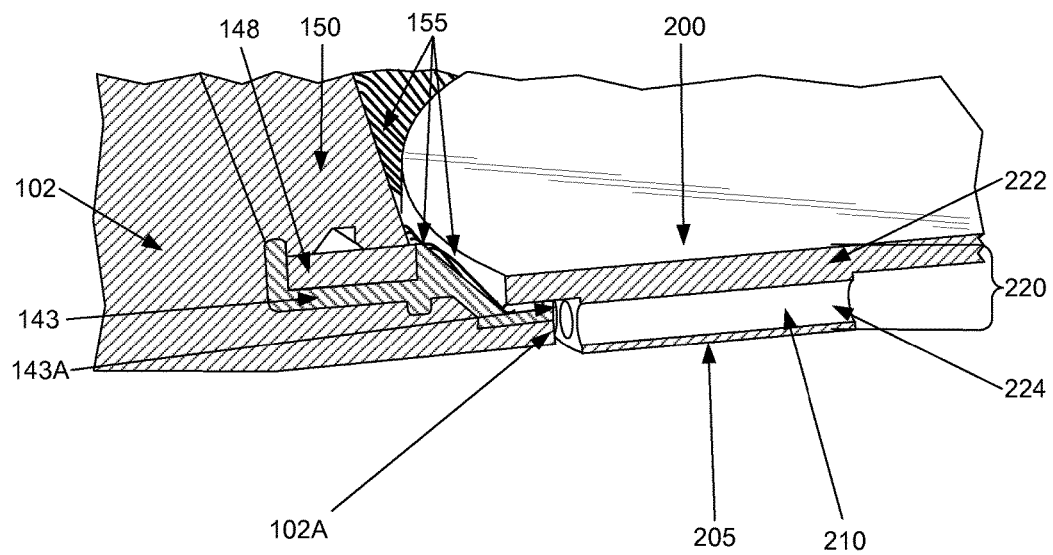
FIG. 2B is a cross-sectional perspective view of a cleaning disc held in a cup/cone clamshell assembly.
Figure 2C:
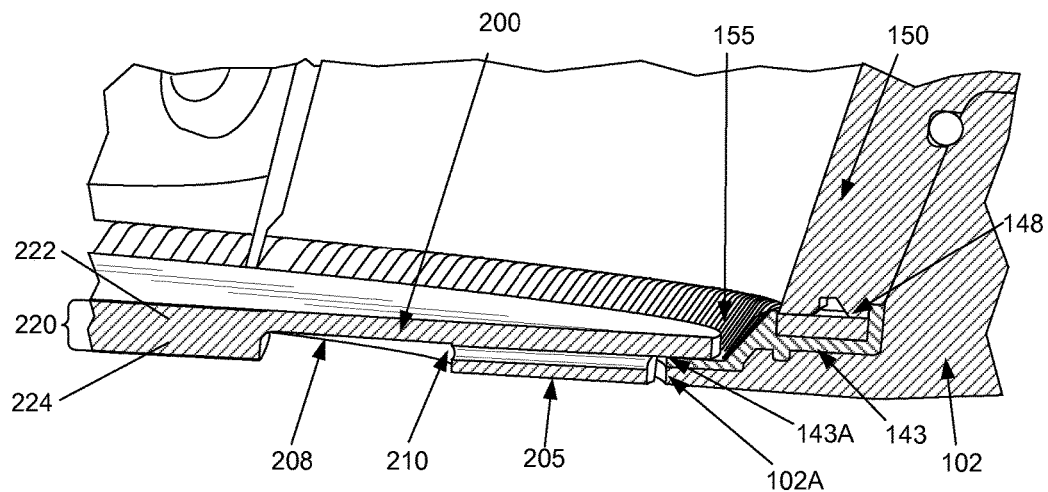
FIG. 2C is another cross-sectional perspective view of a cleaning disc held in a cup/cone clamshell assembly.

FIGS. 2B and 2C illustrate a cleaning disc 200 being held in a substrate holding and processing apparatus which, in this case, is an electroplating apparatus. Visible in both FIGS. 2B and 2C is the cup bottom 102 of the electroplating apparatus, which is typically electrically isolated and, in some embodiments, constructed from plastic. Also visible in FIGS. 2B and 2C is the lip seal 143, the metallic current-carrying contact-backing-plate ring 148, (which in some embodiments is constructed of stainless steel), the metallic current-carrying buss-bar-ring 150 (also oftentimes constructed of stainless steel, depending on the embodiment), and finally the metallic contact member 155. In some embodiments, the metallic contact member 155 is constructed of a corrosion resistant metal having a good spring force for making electrical contact with the semiconductor wafer. Thus, in some embodiments, the metallic contact member 155 may be constructed of a gold or platinum coated stainless steel, or of various Paliney Ag/Pd/Pt alloys such as Paliney 7. As for the spatial configuration of the metallic contact member 155, in some embodiments, the metallic contact member 155 is composed of between 100 and 1000 individual reticulated contact "fingers" which are bent and joined as a continuous strip at one end where they fit between and make a pressure contact to the backing plate ring 148 and buss bar ring 150.

The cleaning disk 200 is placed into the cup 102 and held there in a manner similar to how a semiconductor substrate would be placed and held in the cup 102. In some embodiments, the two sides or faces of the cleaning disc may be symmetrical, but in other embodiments, they may not be symmetrical, and so in these embodiments, whether the cleaning disc is oriented "face up" or "face down" in the cup 102 may make a difference. In some embodiments, the cleaning disc 200 may include a cleaning agent delivery element 210 and possibly a cleaning agent retaining element 205. Collectively, the cleaning agent retaining element 205 and cleaning agent delivery element 210 function to contain the cleaning agent until delivery is appropriate and then deliver it to the elements of the processing apparatus to be cleaned. In certain such embodiments, the elements to be cleaned are the cup bottom 102 and lip seal 143, and the cleaning disc 200 is oriented "face down" in the cup 102 so that the cleaning agent retaining element 205 is oriented "downward" as shown in FIGS. 2B and 2C, and also so that the cleaning agent delivery element 210 coincides with inner periphery of the lip seal 143A and inner periphery of the cup bottom 102A. A seal between the cleaning disc 200 and the inner periphery of the lip seal 143A is made by forcing the disc downward with a cylindrical cone (see cone 103, FIG. 1B) which resides "above" the disc.

In some embodiments, cleaning agent delivery element 210 is a porous region of the cleaning disc, composed of a suitable construction of materials and structure to draw in and retain cleaning agent within its interior by the forces of surface tension and/or adhesion between the cleaning agent and the interior surface of the porous region. In some embodiments, the porous region may be constructed from a sponge or sponge-like material. In other embodiments, the porous region is a solid material having a large number of fine holes. Thus, in some embodiments, a cleaning disc may include a plurality of pores opening at the edge of the cleaning disc 200 and having an interior volume extending into the interior of the disc. In certain such embodiments, these holes or pores may be oriented horizontally, parallel to the upper 230 and lower 240 surfaces of cleaning disc 200, although in other embodiments, the holes/pores may not be quite horizontal, or may have kinks and/or turns making portions of the pores not parallel with the top and bottom surfaces. Although various pore/hole configurations are possible, the holes/pores are typically dimensioned such that a cleaning agent may be retained in the interior of the pores by an adhesive force between the cleaning agent and the interior surface of the pores. Thus, in some embodiments, the interior surfaces of the holes/pores and cleaning agent delivery element 210 (and possibly cleaning agent retaining element 205) are hydrophilic in order to enhance the cleaning agent fluid retention properties of these elements via surface tension interactions and adhesive forces.

In some embodiments, the pores making up the cleaning agent delivery element 210 may be formed by drilling holes into a suitable metallic or thermoplastic material. For example, the holes can be drilled into a corrosion resistant metal such as titanium, or into a hydrophilic thermoplastic such as Ryton. In some embodiments, the holes may have a diameter about or between 0.25 mm and 1.25 mm, or more particularly, about or between 0.5 mm and 1.0 mm, or yet more particularly, about or between 0.7 mm and 0.8 mm. In some embodiments, regions of the cleaning disc 200 other than the cleaning agent delivery element 210 (and possibly the cleaning agent retaining element 205), such as other portions of the disc edge as well as the top and bottom surfaces of the disc may preferably (but not necessarily) be hydrophobic in order to minimize cleaning agent fluid retention in these other regions. For example, a cleaning disc 200 made of titanium or a PPS/Ryton/Techtron type plastic and having drilled holes as the cleaning agent delivery element 210 may be coated with a hydrophobic film everywhere else on the disc, such as at the periphery and/or other interior sections of the disc.

Referring again to FIGS. 2A through 2C, in some embodiments, the cleaning agent delivery element 210 and any associated pores/holes 210 may be located in a substantially circular edge 220 joining the upper 230 and lower 240 surfaces of the disc 200. In some embodiments, this edge 220 has a step built into it so that while a upper portion 222 of the edge 220 is configured to rest on the lip seal 143 of the cup bottom 102, a lower portion 224 of the edge 220 is configured to be adjacent to the inner periphery of the lip seal 143A and cup bottom 102A once the disc 200 is loaded into the holding and processing apparatus. Thus, if the lower portion 224 is configured to deliver cleaning agent via cleaning agent delivery element 210, then when the cleaning disc 200 is loaded "face down" into the holding and processing apparatus, the cleaning agent delivery element 210 will be oriented adjacent to the inner peripheries of the lip seal 143A and cup bottom 102A, as shown in FIGS. 2B and 2C. In configurations having a plurality of pores/holes configured to retain cleaning agent, the pores/holes may have their openings located in the lower portion 224 of edge 220. Thus, the lower portion 224 of edge 220 may have a radius less than that of the upper portion 222. In some embodiments, the lower portion 224 of edge 220 may have a height which is substantially the same height as or somewhat larger than the combined height of the inner peripheries of the lip seal 143A and cup bottom 102A. Thus, in certain such embodiments, for example, the lower portion 224 may be about 2 mm tall. More generally, depending on the embodiment, the mean height of the portion of the edge 220 having pores may be about or between 0.5 mm and 3.5 mm, or more particularly, about or between 1.0 mm and 3.0 mm, or still more particularly, about or between 1.5 mm and 2.5 mm. As indicated above, in some embodiments, the height of the portion of the edge 220 having pores/holes is selected to substantially coincide with the combined height of the inner periphery of the lip seal 143A and the inner periphery of the cup bottom 102A. In some embodiments, the lower portion 224 is located slightly inwards from the inner periphery of the cup bottom 102A and the inner periphery of the lip seal 143A. In certain such embodiments, the lower portion 224 of edge 220 may be located about 1 mm inwards from the 143A and 102A surfaces. Furthermore, so that the upper portion 222 of edge 220 may rest on the cup 102 and lip seal 143 while the lower portion 224 is adjacent to but not physically contacting the inner periphery of the cup 102A and lip seal 143A, the lower portion 224 is located slightly inwards from the upper portion 222—i.e. the radius of the upper portion 222 of edge 220 is slightly larger than the radius of the lower portion 224.

In some embodiments, such as the cleaning disc schematically illustrated in FIG. 2A, there are a large number of individual cleaning agent delivery elements/holes 210 around the circumference of the disc, and there is also an inward chamber 208 slotted radially inwards from the holes 210 (i.e. inward chamber 208 is a continuous slot around the circumference of the disc). Optionally, within the inward chamber 208 is placed an adsorbent element, such as, for example, a wicking fibrous material, or a fabric or cloth, or a filter material, or other suitable material that can wick and retain cleaning agent within the inward chamber 208 of the cleaning disc 200. In principle, as would be understood by one having ordinary skill in the art, any suitable material may be used to form the cleaning agent adsorbent element within inward chamber 208, so long as it is capable of retaining a typically sufficient and/or useful amount of cleaning agent. In certain embodiments, the inward chamber 208 may take the form of an cut out "cavity" annular shaped inward volume, typically between about 0.5 cm and 3 cm in width (viewed radially inwards from the lip seal interface). In one embodiment, the inward chamber 208 is about or between 1 cm and 2 cm in width. In some embodiments, the inward chamber 208 may be an annular shaped region which opens on the bottom surface of the disc. In other embodiments (not shown in FIG. 2A), a portion of inward chamber 208 may be covered by a portion of cleaning agent retaining element 205—i.e. so that a portion of the inward chamber 208 is underneath some portion of the bottom surface of the disc. In certain such embodiments, the inward chamber 208 may be entirely covered by cleaning agent retaining element 205—i.e. so that substantially all (other than perhaps a cleaning agent loading port) is underneath some portion of the bottom surface of the disc. Note, however, that in other embodiments, the cleaning disc 200 may have no inward chamber, and the cleaning agent may just be retained in the large number of azimuthally arranged holes which store the cleaning agent until it is released for cleaning.

In the specific embodiment cleaning disc 200 schematically illustrated in FIG. 2C, the bottom portion 224 of edge 220 is approximately 1.6 mm, and consists of a large number (about 600-700) of roughly equal sized holes having a diameter of approximately 0.76 mm. The holes have been drilled into the bottom portion 224 of edge 220 inwards in the radial direction. Each small hole/pore represents a cleaning agent delivery element 210 functioning to hold and retain cleaning agent by its adhesive force with the cleaning agent and by the cleaning agent's forces of surface tension.

Note that the specific embodiment cleaning disc 200 shown in FIG. 2C is an exemplary embodiment and is presented for explanatory purposes—it should not be construed in any manner which limits the various aspects of the inventions disclosed herein. Cleaning disc 200 presented in FIG. 2C is dimensioned for an inner lip seal having a diameter of about 2.25 mm (which means, for example, that a 300 mm wafer would have an exposed area of diameter 295.5 mm (300 mm-2×2.25 mm). Generally, if holes are used for the cleaning agent delivery elements 210, it is oftentimes useful for the holes 210 to have a diameter of about 3/64 inch (1.2 mm) or less. The choice often depends on the viscosity of the cleaning agent, the amount of cleaning agent needed, and similar factors. In some cases, if the holes are significantly larger, they will not retain the fluid as well, and they may also be unnecessarily larger than the combined height of the lip seal and cup bottom intended to be cleaned. On the other hand, if the holes are very much smaller, e.g. having diameters of less than about 0.25 mm, they will tend to retain the fluid more strongly making it more difficult to extract the fluid and contact it with the intended treatment area as describe in more detail below. Smaller holes may also be more difficult to create by drilling.

Depending on the embodiment, holes may be drilled through the bottom portion of the edge in a straight radially outwards fashion, or drilled with some angle relative to the disc center. In some embodiments, different holes may be drilled with different angles relative to the disc center.

As mentioned above, in some embodiments, the cleaning disc may define an annular inward chamber 208 filled with an adsorbent element which may include a porous structure. The porous structure may include a sintered material, some sponge-like material, or any other porous material which is relatively corrosion resistant and possess pores sized appropriately to hold and retain an appropriate cleaning agent. However, the cleaning agent should optimally not be so strongly retained by the porous material that it cannot be directed to exit the pores without unreasonably high centrifugal forces and/or without requiring excessively high rotation rates in order to free the fluid from the pores (e.g., greater than about 1500 RPM) when appropriate in order to contact the elements to be cleaned. As described in more detail below, in some embodiments, cleaning agent is directed toward the periphery of the cleaning disc 200 by the centrifugal force created upon the spinning of the cleaning disc 200 by the substrate holding and processing apparatus, similarly to how a semiconductor wafer would be spun during an electroplating procedure.

The central inner section of the disc, on the upper surface and/or the lower surface of the cleaning disc 200 can have ribs and/or cross members emanating from the center of the disc to the peripheral cleaning agent retaining areas, in order to improve mechanical rigidity and/or control the flow of the cleaning agent across the disc and into the cleaning agent retaining areas (for example, in embodiments where the pores 210 are filled by application of the cleaning agent to the center of the disc followed by rotation, the ribs or cross members are on the same surface as pores 210 and direct fluid into those pores.

Thus, a cleaning disc can be preloaded with a cleaning agent, loaded into a substrate holding and processing apparatus, and then spun in order to dispense the cleaning agent selectively to the periphery of the cleaning disc, thereby cleaning the elements of the processing apparatus proximate to the cleaning disc's periphery. Various embodiment methods of cleaning elements of a substrate holding and processing apparatus, and in particular an electroplating apparatus, are described in more detail below which utilize the cleaning discs disclosed herein. Also disclosed are methods employing robotic wafer handlers and the like. Plating tools employing such methods are sold under the trade name "Sabre™ 3D tools," available from Novellus Systems, of San Jose, Calif.

Also disclosed herein are methods of cleaning one or more elements of a semiconductor holding and processing apparatus. In some embodiments, the one or more elements to be cleaned include the cup bottom and lip seal of the processing apparatus, and in some embodiments, the cleaning methods utilize a cleaning disc as described above. Some of the cleaning methods disclosed herein are described in reference to, and may be employed in the context of, an automated tool-integrated approach. However, it should be understood that those skilled in the art would appreciate that other approaches, including approaches involving manual operations, can also be performed or substituted to accomplish some or all of the operations described below. Accordingly, although embodiment methods are described in the context of an automated integrated tool approach and, in particular, the automated wafer plating tool apparatus 300 illustrated in FIG. 3, a more general approach is also being disclosed as schematically illustrated by the flowchart of FIG. 4.

Figure 3:
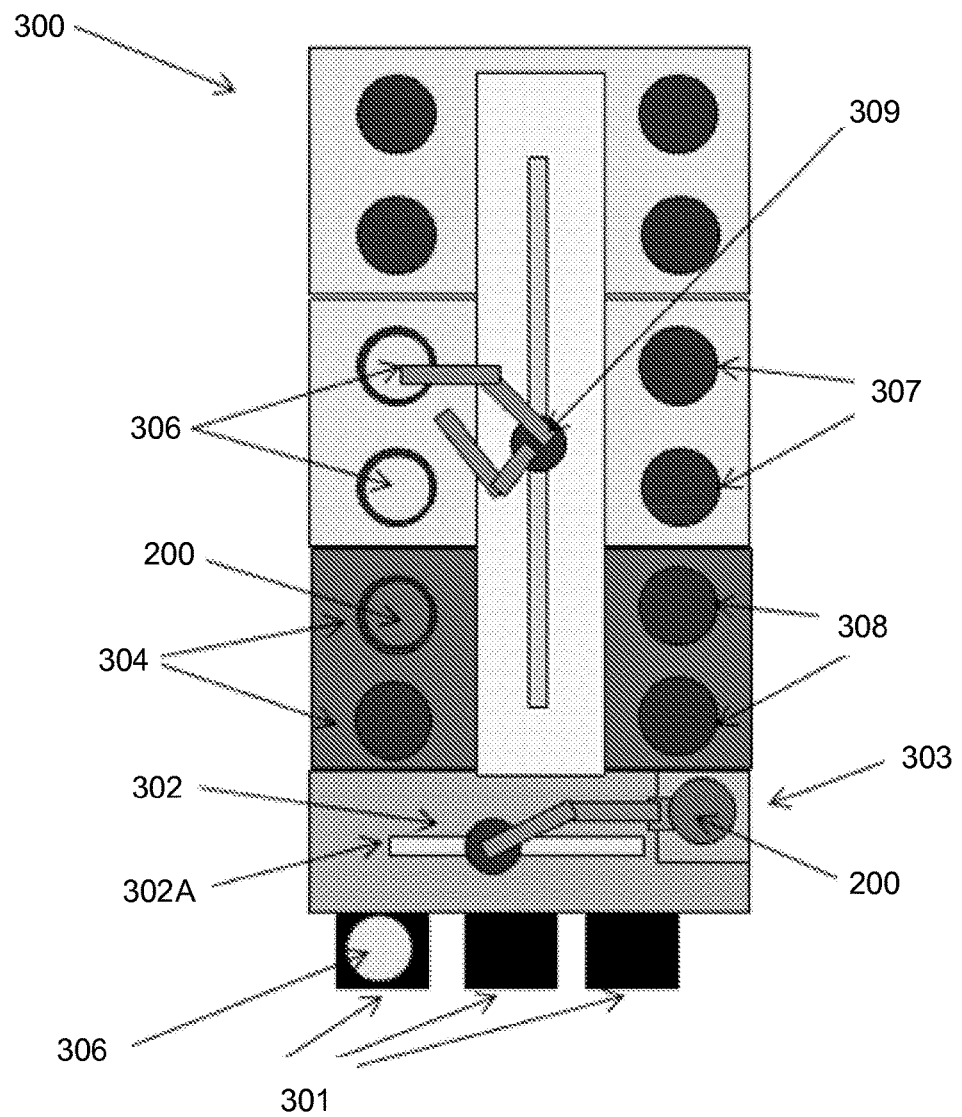
FIG. 3 is a schematic drawing of one suitable automated substrate plating tool apparatus.
Figure 4:
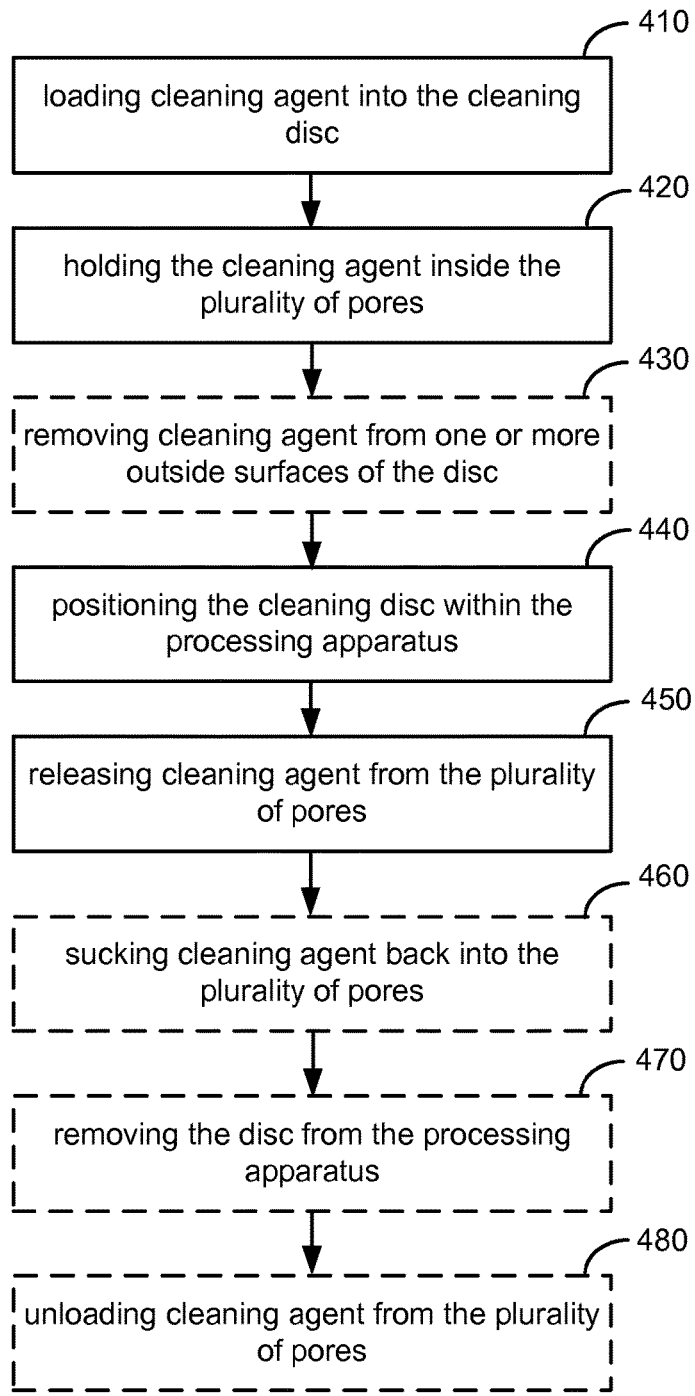
FIG. 4 is a flow chart that outlines a variety of embodiment methods disclosed herein.

Reference is now made to FIG. 3, which is a schematic drawing of one suitable automated wafer plating tool apparatus 300 configured to plate a semiconductor wafer (e.g. silicon) or similar substrate (glass coated thinned wafer, GaAs, ceramic, etc.) with various metals and alloys (e.g. copper, nickel, gold, palladium, cobalt, indium, tin, lead, lead-tin, tin-silver, FeCo), and perform other necessary plating sub-processes (e.g. spin rinsing and drying, metal and silicon wet etching, electroless deposition, pre-wetting and pre-chemical treating, photoresist stripping, surface pre-activation). The automated wafer plating tool apparatus is shown schematically looking top down in FIG. 3, and only a single level or "floor" is revealed in the Figure, but it is readily understood by one of ordinary skill in the art that such an apparatus, e.g. the Novellus Sabre™ 3D tool, can have two or more levels "stacked" on top of each other, each potentially having identical or different types of processing stations.

As mentioned above, in some embodiments, contamination in the scenario of tin-silver solder alloy plating is of particular interest because it is known these scenarios generally have the problem of creating spurious metal deposits on and around the wafer holding cup and lip seal over time. Accordingly, oftentimes with repeated use periodic maintenance is required to remove and clean the metallic deposits and other film buildup. Furthermore, since spuriously plated metal deposits on the sealing area and its vicinity divert current and otherwise change the intended pattern of current distribution, removal of these deposits is desired to maintain good within wafer uniformity and particle performance.

Referring again to FIG. 3, the wafers 306 that are to be processed are generally feed to the automated plating tool 300 through a front end loading "foup" 301 and, in this example, are brought from the foup to the main wafer processing area of the tool via a front-end robot 302 that can retract and move a wafer in multiple dimensions from one station to another of the accessible stations—two front-end accessible cleaning agent loading stations 304 and also two front-end accessible spin rinse drying (SRD) stations 308 are shown in this example. Also shown in the example are two tin-silver alloy plating cells 307. Lateral movement from side to side of the front-end robot 302 is accomplished utilizing robot track 302A.

In some embodiments, a cleaning method 400, as schematically illustrated in FIG. 4, is initiated as follows. A data processing system within or connected to the automated plating tool 300 tracks the plating of wafers 306 by the tin-silver alloy plating cell 307, and when the data processing system determines that cleaning the plating cell 307 is necessary and/or desirable (e.g. typically after 50 to 200 wafers or more have been plated, depending on the deposition rate and charge passed per wafer), the system initiates an automated cleaning process. First, the system designates as temporarily unavailable the stations to be cleaned—e.g. the two plating cells 307. Once so designated, further plating in plating cells 307 is postponed until the cleaning operation is completed. Note that in a manual cleaning process, the plating cells 307 would need to be denoted by an operator as having completed the manual cleaning operation before plating could be resumed, but in the automated process, the data processing system initiates cleaning and, when complete, designates plating cells 307 available for plating once again, and thereafter until the predesignated cleaning interval arises or some other criteria is again met.

Once initiated, in some embodiments, a cleaning method 400 proceeds as follows. First, again referring to FIG. 3, the automated wafer plating tool apparatus 300 uses front-end robot 302 to extract a cleaning disc 200 from the cleaning disc storage area 303 and place the cleaning disc in one of the two cleaning agent loading stations 304. (Note that in tools such as the Novellus Sabre™ 3D plating tool where operations are run in cell pairs—or Duets—the two cell modules of each Duet operate at the same time, so a step in the cleaning sequence will not begin until both Duets are ready.)

Next, cleaning agent is loaded into the cleaning disc 200 (see step 410 of FIG. 4). In some embodiments, the cleaning agent may be stored at a cleaning agent loading station 304 within the automated wafer plating tool apparatus 300, which may reside, for example, on the plating tool's left front and upper deck. Within the cleaning agent loading station 304, a suitable volume of cleaning agent may be stored in a dosing size like bottle. In one embodiment, the cleaning disc is placed "face up" in a cleaning agent loading station 304 which contains a disc supporting chuck that can apply cleaning agent to the cleaning disc 200 by, for example, generally delivering a stream or spray to the disc face and having the cleaning agent flow radially outwards due to viscous forces from simultaneously rotating the disc. The disc is held "face up" while cleaning agent is applied and the disc is held in a wafer holding chuck and spun at about or between 50 and 300 RPM. In some embodiments, this method of application is designed so as to avoid getting cleaning agent onto the backside of the cleaning disc and potentially subsequently contaminating the tool's robotic wafer/disc handling arm or other elements. Note that the "face" of the cleaning disc is the side of the disc having the cleaning fluid delivery elements (e.g. the surface with the protrusion having cleaning agent retaining element 205, see FIG. 2A) and what is referred to as the lower surface or back of the cleaning disc is the other side, which in some embodiments, comprises a substantially flat surface. "Face up" therefore refers to the disc orientation of the "face" away from the center of the earth, and "face down" refers to the "face" oriented towards the center of the earth. Thus, while supplying fluid and spinning the cleaning disc face up in the cleaning agent loading station, the process fills the disc cleaning periphery fluid retention region as the spray or stream of the cleaning agent is applied to the general center of the disc face of the cleaning disc, builds up and move outwards. As the disk spins the cleaning agent is retained on the general face of the disc by gravity and move radially outwards as it is spun, filling the cleaning agent storage and delivery elements 210, e.g. the holes/pores, with cleaning chemical Excess cleaning agent passes over the cleaning agent delivery elements 210 while the elements 210 (e.g. the drilled holes/pores) fill and retain the cleaning agent. The rotational speed and size of the holes/pores may be optimized to allow retention of cleaning agent within the holes/pores while allowing the excess cleaning agent to flow off the disc. Once the cleaning agent delivery elements 210 are filled, the flow may be stopped and the appropriate rotation speed is applied, removing excess fluid, so that the disc is essentially free of cleaning agent except in the cleaning agent delivery elements 210 of the disc (e.g. the drilled holes/pores). In other embodiments, cleaning agent is loaded into the cleaning disc 200 (step 410 of FIG. 4) by immersing the cleaning disc 200 into a tank containing the cleaning agent. Depending on the embodiment, the cleaning disc may only be partially immersed, but in any event, it is immersed to an extent sufficient to allow cleaning agent to be drawn into the cleaning agent delivery elements 210 of the cleaning disc 200—for instance, by capillary action. Of course, the cleaning agent delivery element 210 may take the form of drilled holes or pores, or it may be composed of a porous sintered material as described above in reference to FIGS. 2A through 2C. In either of these exemplary embodiment methods, the cleaning agent is loaded into the cleaning disc (step 410) by receiving the cleaning agent into the cleaning agent delivery elements 210 of the cleaning disc where it is held (step 420) until needed. In some embodiments, the cleaning agent is held (step 420) in the cleaning disc by adhesion to the interior surfaces of the plurality of pores.

In some embodiment methods, the loading of the cleaning agent into the cleaning disc (step 420) is followed by a step of removing cleaning agent from one or more outside surfaces of the disc (step 430), typically prior to the next step in the cleaning method (e.g. the positioning step 440). In some embodiments, such as described above, cleaning agent is removed simply by stopping the flow of cleaning agent during the loading step 420 and allowing the cleaning disc to continue rotating so that the remaining cleaning agent flows off the surface of the disc. In certain embodiments, the rate of rotation may be increased to promote shedding of the cleaning agent once the flow of cleaning agent has been stopped, however, the rotation rate would not typically be increased to the point where cleaning agent flows out of the pores/holes. Even if application of cleaning agent is not accompanied by spinning the cleaning disc, during the step of removing cleaning agent (step 430), spinning may still be employed to promote removal of cleaning agent, and, similarly, a selected rotation rate would typically be sufficiently fast to cause any cleaning agent remaining on the outside surfaces to flow off the disc, but sufficiently slow such that cleaning agent within the disc's plurality of pores substantially remains within the plurality of pores. In certain such embodiments, this rotation rate is about or between 50 RPM and 250 RPM for a period of 5 to 60 seconds.

In some embodiments, the removal of cleaning agent from the outside surface (step 430) may include rinsing one or more outside surfaces with a rinsing agent. In certain such embodiments, the rinsing is accompanied by spinning as described above, and in certain embodiments spinning may not be necessary. If the disc is spun, selection of a rinsing agent with a viscosity less than the cleaning agent may help promote the selection of a suitable spin rate. In some embodiments, water or distilled and deionized water may serve as a suitable rinsing agent. Thus, in some embodiments, water may be applied to the outside surfaces of the cleaning disc for a short time while the cleaning disc is rotated at a suitably slow speed so as to aid in the flushing of the outside surfaces of excess cleaning agent, and thereafter, excess cleaning fluid entrained on the outside surfaces of the disk may be removed by spinning the disc at an appropriate higher speed so that fluid remains in the plurality of pores but flows off of the main outside surfaces. Alternatively or in addition to these steps, forced air drying may be employed to remove any excess cleaning agent or rinsing agent. As a result of one of the above embodiment removal steps (step 430), the pores/holes of the cleaning disc are filled with cleaning agent, but the surfaces of the cleaning disc are substantial free of the same. At this point, cleaning agent will then be held in the cleaning disc (step 440) until it is appropriate for it to be released for contacting the one or more elements of the apparatus to be cleaned.

Once cleaning agent has been loaded (step 410) and held (step 420) in the cleaning agent delivery elements 210 of the cleaning disc 200, and any removal or rinsing has been performed (step 430), the cleaning disc is positioned in the processing apparatus (step 440) so that it may be used to clean various elements of the processing apparatus. In some embodiments, the cleaning disc 200 is transported by the back end robot 309 to tin-silver alloy plating station 307, and inserted into the clamshell of plating station 307 similar to as illustrated above in FIGS. 2A and 2B. In some embodiments, the cleaning disc 200 is specifically positioned within the processing apparatus (step 440) such that a plurality of pores/holes in the cleaning disc holding cleaning agent are adjacent to the one or more elements to be cleaned (which would normally be adjacent to a semiconductor wafer, when a wafer is held in the clamshell assembly). As with the front end robot 302, the back end robot 309 is also shown positioned on a track and is capable of transporting either semiconductor wafer or cleaning disc 200 from the forward cleaning agent loading station 304 to any of the upper or lower decks of the processing tool 300, and to any processing station throughout the processing tool 300. Once the back end robot 309 places the cleaning agent holding cleaning disc 200 into the cup (see 102, FIGS. 1B, 2A, and 2B), the cone (103, FIG. 1B) is lowered, closing the wafer holding clamshell (cup and cone), and forming a seal between the edge of the cleaning disc 200 and the lip seal 143 (FIGS. 1B, 2A, and 2B).

Once the cleaning disc 200 is positioned within the processing apparatus, a step 450 of releasing cleaning agent from the disc's cleaning agent delivery elements is performed. In some embodiments, the cleaning agent is released from a plurality of pores such that the one or more elements of the apparatus to be cleaned are contacted by the released cleaning agent. In some embodiments, this is accomplished by spinning the clamshell and cleaning disc at an appropriate rotational rate to force out cleaning agent from the plurality of pores/holes (by, e.g., centrifugal forces overcoming forces of surface tension and/or adhesion) so as to contact and wet the inner periphery of the lip seal 143A and the cup bottom 102A, but not to allow, for example, the substantially continuous flow of cleaning agent out of the plurality of pores/holes and off of the disc and cup bottom. Suitable rotation rates range from about 50 to about 500 RPM depending on the hole sizes, the surface tension of the cleaning agent, the strength of the adhesion between the cleaning agent and the various surfaces of the cup bottom and lip seal, the viscosity of the cleaning agent, and the size of the gap separating the pores/holes from the inner peripheries of the lip seal 143A and cup bottom 102A. Rotation of the cleaning disc is continued so that the inner periphery of the lip seal and cup bottom are exposed and contacted with the cleaning chemical generally anywhere from 10 seconds to 3 minutes, largely depending on the strength of the cleaning agent and the amount of spurious metal deposit and buildup. Accordingly, in some embodiments, the one or more elements of the processing apparatus to be cleaned may be contacted with cleaning agent for about 1 second, 5 seconds, 10 seconds, 20 seconds, 30 seconds, 1 minute, 2 minutes, 2.5 minutes, 3 minutes, or 3.5 minutes, or, in some embodiments, a range of contact times may be appropriate, such as any range defined by any pair of the aforementioned contact times. Thus, for example, an appropriate range of contact times may be from 1 second to 3.5 minutes, or from 5 seconds to 30 seconds, or from 30 seconds to 3 minutes.

Thereafter, in some embodiments, before the cleaning disc is removed from the clamshell, the cleaning disc is spun at a sufficiently high rate (e.g., greater than 500 RPM) to remove the cleaning agent from the gap separating the cleaning agent delivery elements 210 from the lip seal and cup bottom. In some embodiments, spent cleaning agent will then flow radially outward along the bottom of the cup surface and into a waste collection area of the plating cell. This is followed optionally by a distilled deionized water rinsing step with the cleaning disk spinning at sufficiently high speed so as to flush the pores of the disc and the aforementioned gap of cleaning agent with water.

In other embodiments, before the cleaning disc is removed from the clamshell, reduction in the rotation rate causes some or a majority of the cleaning agent to be sucked back into the pores/holes (step 460). Afterwards, the cleaning disc may be removed from the clamshell and processing apparatus (step 470). Optionally, after removal of the cleaning disc, a flat or blanket "dummy" non-functioning-device wafer is drawn from the dummy wafer storage area 303 and placed into the clamshell after the above cleaning operation, and the lip seal assembly is rinsed with distilled deionized water with the blanket dummy wafer in the clamshell, so as to remove residual cleaning agent from the lip seal. This can be followed optionally by a cup and cone rinsing (CCR) operation so as to clean the lip seal, cup internals such as electrical contacts, and the cone interfaces.

In some embodiments, after removal from the clamshell of the processing apparatus which was cleaned, the cleaning disc 200 is moved (e.g., by back end robot 309) to a spin rinse drying (SRD) station 308, where any remaining cleaning agent may be unloaded from the cleaning agent delivery elements 210 (step 480). In some embodiments, the cleaning disc may be first optionally spun (e.g. face up or face down while held in a wafer holding chuck at a high speed, e.g. 500-2000 RPM) to remove most of the entrained cleaning agent held in the pores/holes of the disc. In some embodiments, this spin operation is then followed by one or more water dispensing and pore/hole flushing/absorption/rinsing steps and drying/spinning steps so as to flush any remaining cleaning agent out of the disc pores and also from the disc surface.

In some embodiments, the disc undergoes a high speed (e.g. 1000 to 2000 RPM) drying step to remove all fluids from the disc surfaces and fluid retaining pores/holes/elements. After this, the cleaning disc is extracted by the front end robot 302 and returned dry to the dummy wafer storage area 303 for reuse at a later time.

Finally, note that the foregoing disclosed cleaning apparatuses and cleaning methods may be employed as part of an autocleaning procedure used in a method of processing a series of semiconductor substrates. Methods of electroplating a sequence of substrates employing an autocleaning procedure are described in U.S. Provisional Patent Application No. 61/676,841, filed Jul. 27, 2012, titled "METHODS AND SYSTEMS FOR CLEANING ELECTROPLATING SUBSTRATE HOLDERS," which is hereby incorporated by reference in its entirety herein for all purposes. Thus, for instance, a method of electroplating a sequence of semiconductor wafers employing an autocleaning step, may utilized the cleaning discs and cleaning methods disclosed herein during the autocleaning step. Various factors potentially considered when deciding whether initiation of a sequence of automated cleaning steps is warranted are described in detail in the foregoing provisional US patent application, such as, for example, whether a predetermined number of wafers have been plated since the last cleaning.

Although the foregoing embodiments have been described in some detail for purposes of clarity and understanding, it will be apparent to one of ordinary skill in the art that certain changes and modifications may be practiced. Therefore, the disclosed embodiments are to be viewed as illustrative rather than restrictive, and the breadth of this disclosure is not to be limited in scope to the specific details provided herein but rather may be modified within the appropriate scope and equivalents as would be understood by one of ordinary skill in the art.

We claim:

1. A method of cleaning one or more elements of a semiconductor holding and processing apparatus, the method comprising:
    loading a cleaning agent into a cleaning disc by receiving the cleaning agent into a plurality of pores opening in one or more edges of the disc, said pores extending into interior surfaces of the disc;
    retaining the cleaning agent inside the plurality of pores;
    positioning the cleaning disc within the semiconductor holding and processing apparatus such that the plurality of pores are adjacent to the one or more elements of the apparatus to be cleaned, the one or more elements to be cleaned normally being adjacent to a semiconductor wafer when a wafer is held in the processing apparatus for processing; and
    cleaning the one or more elements of the semiconductor holding and processing apparatus by releasing the cleaning agent from the plurality of pores such that the one or more elements of the apparatus to be cleaned are contacted by the released cleaning agent.

2. The method of claim 1, wherein the method of cleaning is used to clean a semiconductor holding and processing apparatus after the apparatus has been used to electroplate a semiconductor wafer.

3. The method of claim 1, further comprising:
    removing the cleaning agent from one or more outside surfaces of the disc, after said loading but prior to said positioning;
wherein the removing of the cleaning agent comprises spinning the disc at a rotation rate such that the cleaning agent flows off one or more outside surfaces of the disc, but the cleaning agent substantially remains within the plurality of pores.

4. The method of claim 1, further comprising:
    removing the cleaning agent from one or more outside surfaces of the disc, after said loading but prior to said positioning;
wherein the removing of the cleaning agent comprises rinsing one or more outside surfaces of the disc with a rinsing agent and spinning the disc at a rotation rate such that rinsing agent flows off of the one or more outside surfaces of the disc, but the cleaning agent substantially remains within the plurality of pores.

5. The method of claim 1, wherein the loading of the cleaning agent further comprises:
    immersing a portion of the disc in the cleaning agent; and
    drawing the cleaning agent into the pores by capillary action.

6. The method of claim 1, wherein the retaining of the cleaning agent further comprises:
    adhering the cleaning agent to the interior surfaces of the plurality of pores.

7. The method of claim 1, wherein the releasing of the cleaning agent from the plurality of pores comprises spinning the disc at a rotation rate such that the one or more elements to be cleaned are contacted by the released cleaning agent, but the released cleaning agent does not substantially flow continuously out of the plurality of pores.

8. The method of claim 1, wherein the one or more elements to be cleaned comprises a lip seal and a cup bottom of a semiconductor holding and processing apparatus.

9. The method of claim 1, wherein the cleaning agent comprises an acid.

10. The method of claim 1, wherein the cleaning agent is a metal complexing agent.

11. The method of claim 1, wherein the plurality of pores have substantially circular openings with diameters about or between 0.25 mm and 1.25 mm.

12. The method of claim 1, wherein the plurality of pores extend into the interior surfaces of the cleaning disc in between a substantially non-porous portion of an upper surface of the disc and a substantially non-porous portion of a lower surface of the disc.

13. The method of claim 1, wherein at least one of the edges of the cleaning disc in which the plurality of pores open comprises:
 a substantially circular upper portion joined to an upper surface of the disc; and
 a substantially circular lower portion joined to a lower surface of the disc, the lower portion having a radius less than the radius of the upper portion;
wherein the openings of the plurality of pores open in the lower portion of the edge.

14. The method of claim 3, wherein the rotation rate is about or between 50 RPM and 250 RPM.

15. The method of claim 4, wherein a viscosity of the rinsing agent is less than a viscosity of the cleaning agent.

16. The method of claim 7, further comprising sucking the cleaning agent back into the plurality of pores, after being released to contact the one or more elements to be cleaned in said releasing, wherein the suction is created by reducing the rotation rate of the disc relative to said releasing.

17. The method of claim 8, wherein the released cleaning agent removes metal deposits from the one or more elements to be cleaned.

18. The method of claim 9, wherein the acid is nitric acid having a concentration in the cleaning agent of about 10% or more by weight.

19. The method of claim 12, wherein the plurality of pores have substantially circular openings with diameters about or between 0.25 mm and 1.25 mm.

20. The method of claim 13, wherein the disc further comprises a cleaning agent adsorbent element located within a chamber radially inward from the plurality of pores, the adsorbent element configured to supply cleaning agent to the plurality of pores.

21. The method of claim 16, further comprising:
 removing the disc from the semiconductor holding and processing apparatus; and
 unloading the cleaning agent from the plurality of pores by spinning the disc at a rotation rate of about or greater than 500 rpm.

22. The method of claim 17, wherein the metal deposits comprise an alloy of tin and/or an alloy of indium.

* * * * *